US008940147B1

(12) United States Patent
Bartsch et al.

(10) Patent No.: US 8,940,147 B1
(45) Date of Patent: Jan. 27, 2015

(54) MICROFLUIDIC HUBS, SYSTEMS, AND METHODS FOR INTERFACE FLUIDIC MODULES

(75) Inventors: Michael S. Bartsch, Menlo Park, CA (US); Mark R. Claudnic, Livermore, CA (US); Hanyoup Kim, Rockville, MD (US); Kamlesh D. Patel, Dublin, CA (US); Ronald F. Renzi, Tracy, CA (US); James L. Van De Vreugde, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 393 days.

(21) Appl. No.: 13/456,135

(22) Filed: Apr. 25, 2012

Related U.S. Application Data

(60) Provisional application No. 61/478,641, filed on Apr. 25, 2011.

(51) Int. Cl.
*G01N 27/447* (2006.01)
(52) U.S. Cl.
USPC ............................ 204/601; 422/502; 422/504
(58) Field of Classification Search
USPC ........................... 204/451, 601; 422/502, 504
See application file for complete search history.

(56) References Cited

U.S. PATENT DOCUMENTS

| 6,989,234 | B2 | 1/2006 | Kolar et al. |
|---|---|---|---|
| 7,329,545 | B2 | 2/2008 | Pamula et al. |
| 7,439,014 | B2 | 10/2008 | Pamula et al. |
| 7,569,129 | B2 | 8/2009 | Pamula et al. |
| 7,727,723 | B2 | 6/2010 | Pollack et al. |
| 7,763,471 | B2 | 7/2010 | Pamula et al. |
| 7,815,871 | B2 | 10/2010 | Pamula et al. |
| 7,816,121 | B2 | 10/2010 | Pollack et al. |
| 7,822,510 | B2 | 10/2010 | Paik et al. |
| 7,851,184 | B2 | 12/2010 | Pollack et al. |

FOREIGN PATENT DOCUMENTS

WO     WO 2012/040227 A1 *   4/2010

OTHER PUBLICATIONS

Abdelgawad, M. et al., "All-terrain droplet actuation", Lab on a Chip, 2008. 8(5): p. 672-677.
Abdelgawad, M. et al., "The Digital Revolution: A New Paradigm for Microfluidics", Advanced Materials, 2009. 21(8): p. 920-925.
Barbulovic-Nad, I. S. et al., "A microfluidic platform for complete mammalian cell culture", Lab on a Chip, 2010. 10(12): p. 1536-1542.

(Continued)

*Primary Examiner* — J. Christopher Ball
(74) *Attorney, Agent, or Firm* — Helen S. Baca

(57) ABSTRACT

Embodiments of microfluidic hubs and systems are described that may be used to connect fluidic modules. A space between surfaces may be set by fixtures described herein. In some examples a fixture may set substrate-to-substrate spacing based on a distance between registration surfaces on which the respective substrates rest. Fluidic interfaces are described, including examples where fluid conduits (e.g. capillaries) extend into the fixture to the space between surfaces. Droplets of fluid may be introduced to and/or removed from microfluidic hubs described herein, and fluid actuators may be used to move droplets within the space between surfaces. Continuous flow modules may be integrated with the hubs in some examples.

21 Claims, 17 Drawing Sheets

(56) References Cited

OTHER PUBLICATIONS

Chang, Y. H. et al., "Integrated polymerase chain reaction chips utilizing digital microfluidics", Biomedical Microdevices, 2006. 8(3): p. 215-225.
Cho, S. K. et al., "Concentration and binary separation of micro particles for droplet-based digital microfluidics", Lab on a Chip, 2007. 7(4): p. 490-498.
Fair, R. B. et al., "Chemical and biological applications of digital-microfluidic devices", IEEE Design & Test of Computers, 2007. 24(1): p. 10-24.
Fair, R. B., "Digital Microfluidics: is a true lab-on-a-chip possible?", Microfluidics and Nanofluidics, 2007. 3(3): p. 245-281.
Fan, S. -. et al., "General digital microfluidic platform manipulating dielectric and conductive droplets by dielectrophoresis and electrowetting", Lab on a Chip, 2009: p. 1236-42.
Fouillet, Y. et al., "Digital microfluidic design and optimization of classic and new fluidic functions for lab on a chip systems", Microfluidics and Nanofluidics, 2008. 4(3): p. 159-165.
Gong, J. et al., "Direct-referencing two-dimensional-array digital microfluidics using multilayer printed circuit board", Journal of Microelectromechanical Systems, 2008. 17(2): p. 257-264.
Gong, J. et al., "Portable digital microfluidics platform with active but disposable lab-on-chip", Mems 2004: 17th Ieee International Conference on Micro Electro Mechanical Systems, Technical Digest, 2004: p. 355-358.
Gong, J. et al., "All-electronic droplet generation on-chip with real-time feedback control for EWOD digital microfluidics", Lab on a Chip, 2008. 8(6): p. 898-906.
Gorbatsova, J. et al., "Digital Microfluidic Sampler for a Portable Capillary Electropherograph", Analytical Chemistry, 2009. 81(20): p. 8590-8595.
Hua, Z. S. et al., "Multiplexed Real-Time Polymerase Chain Reaction on a Digital Microfluidic Platform", Analytical Chemistry, 2010. 82(6): p. 2310-2316.
Luo, J. K. et al., "Moving-part-free microfluidic systems for lab-on-a-chip", Journal of Micromechanics and Microengineering, 2009. 19(5): p. 054001 (14 pp.)-054001 (14 pp.).
Malic, L. T. et al., "Biochip functionalization using electrowetting-on-dielectric digital microfluidics for surface plasmon resonance imaging detection of DNA hybridization", Biosensors & Bioelectronics, 2009. 24(7): p. 2218-2224.
Malic, L. T. et al., "Two-dimensional droplet-based surface plasmon resonance imaging using electrowetting-on-dielectric microfluidics", Lab on a Chip, 2009. 9(3): p. 473-475.
Miller, E. M. et al., "Digital bioanalysis", Analytical and Bioanalytical Chemistry, 2009. 393(2): p. 419-426.
Moon, H. et al., "An integrated digital microfluidic chip for multiplexed proteomic sample preparation and analysis by MALDI-MS", Lab on a Chip, 2006. 6(9): p. 1213-1219.
Moon, H. et al., "Low voltage electrowetting-on-dielectric", Journal of Applied Physics; vol. 92, No. 1; Oct. 1, 2002, pp: 4080-4087.
Nelson, W. et al., "An EWOD droplet microfluidic chip with integrated local temperature control for multiplex proteomics", 2009 IEEE 22nd International Conference on Micro Electro Mechanical Systems. MEMS 2009, 2009: p. 280-3.
Nelson, W. et al., "Incubated Protein Reduction and Digestion on an Electrowetting-on-Dielectric Digital Microfluidic Chip for MALDI-MS", Analytical Chemistry, 2010. 82(23): p. 9932-9937.
Nichols, K. P. et al., "A digital microfluidic system for the investigation of pre-steady-state enzyme kinetics using rapid quenching with MALDI-TOF mass spectrometry", Analytical Chemistry, 2007. 79: p. 8699-8704.
Paik, P. Y. et al., "Adaptive cooling of integrated circuits using digital microfluidics", IEEE Transactions on Very Large Scale Integration (Vlsi) Systems, 2008. 16(4): p. 432-443.
Schaller, V. et al., "Towards an electrowetting-based digital microfluidic platform for magnetic immunoassays", Lab on a Chip, 2009. 9(23): p. 3433-3436.
Shah, G. J. et al., "EWOD-driven droplet microfluidic device integrated with optoelectronic tweezers as an automated platform for cellular isolation and analysis", Lab on a Chip, 2009. 9(12): p. 1732-1739.
Shah, G. J. et al., "High-purity separation of rare species in droplet microfluidics using droplet-conduit structures", IEEE 22nd International Conference on Micro Electro Mechanical Systems. MEMS 2009. Sorrento, Italy.
Sista, R., "Development of a digital microfluidic platform for point of care testing", Lab on a Chip, 2008. 8(12): p. 2091-2104.
Sista, R. S. et al., "Heterogeneous immunoassays using magnetic beads on a digital microfluidic platform", Lab on a Chip, 2008. 8(12): p. 2188-2196.
Srinivasan, V. et al., "A digital microfluidic biosensor for multianalyte detection", Mems-03: Ieee the Sixteenth Annual International Conference on Micro Electro Mechanical Systems, 2003: p. 327-330.
Srinivasan, V. et al., "An integrated digital microfluidic lab-on-a-chip for clinical diagnostics on human physiological fluids", Lab on a Chip, 2004. 4(4): p. 310-315.
Teh, S. Y. et al., "Droplet Microfluidics.", Lab on a Chip, 2008. 8(2): p. 198-220.
Ugsornrat, K. et al., "Simulation and Experimental Study of Electrowetting on Dielectric (EWOD) Device for a Droplet Based Polymerase Chain Reaction System, in 13th International Conference on Biomedical Engineering, vols. 1-3", C.T. Lim and J.C.H. Goh, Editors. 2009, Springer: New York. p. 859-862.
Wang, Y. et al., "Efficient in-droplet separation of magnetic particles for digital microfluidics", Journal of Micromechanics and Microengineering, 2007. 17(10): p. 2148-2156.
Watson, M. W. et al., "Multilayer Hybrid Microfluidics: A Digital-to-Channel Interface for Sample Processing and Separations", Analytical Chemistry, 2010. 82(15): p. 6680-6686.
Wheeler, A. R. et al., "Digital microfluidics with in-line sample purification for proteomics analyses with MALDI-MS", Analytical Chemistry, 2005. 77(2): p. 534-540.
Xu, T. et al., "Automated, accurate, and inexpensive solution-preparation on a digital microfluidic biochip", BioCAS 2008. IEEE Biomedical Circuits and Systems Conference—Intelligent Biomedical Systems, 2008: p. 301-4.
Yang, H. et al., "A World-to-Chip Interface for Digital Microfluidics", Analytical Chemistry, 2009. 81(3): p. 1061-1067.
Yang, H., "Connecting interface for modularization of digital microfluidics", Proceedings of the SPIE—The International Society for Optical Engineering, 2008: p. 68860L-1-12.
Yi, U. C. et al., "Soft printing of droplets pre-metered by electrowetting", Sensors and Actuators A—Physical, 2004. 114(2-3): p. 347-354.
Zhao, Y. J. et al., "Droplet manipulation and microparticle sampling on perforated microfilter membranes", Journal of Micromechanics and Microengineering, 2008. 18(2): p. 11.
Zhao, Y. J. et al., "Microparticle sampling by electrowetting-actuated droplet sweeping", Lab on a Chip, 2006. 6(1): p. 137-144.
Au, S. H. et al., "A New Angle on Pluronic Additives: Advancing Droplets and Understanding in Digital Microfluidics", Langmuir, 2011. 27: p. 8586-8594.
Boles, D. J. et al., "Droplet-Based Pyrosequencing Using Digital Microfluidics", Analytical Chemistry, 2011. 83: p. 8439-8447.
Coupland, P., "Microfluidics for the upstream pipeline of DNA sequencing—a worthy application?", Lab on a Chip, 2010. 10: p. 544-547.
Jebrail, M. J. et al., "Combinatorial Synthesis of Peptidomimetics Using Digital Microfluidics", Journal of Flow Chemistry, 2012. 2(3): p. 103-107.
Jebrail, M. J. et al., "Digital microfluidics: a versatile tool for applications in chemistry, biology and medicine", Lab on a Chip, 2012. 12: p. 2452-2463.
Jebrail, M. J. et al., "Digital Microfluidics for Automated Proteomic Processing", Journal of Visualized Experiments, 2009. 33: e1603 (5 pages).

(56) References Cited

OTHER PUBLICATIONS

Jebrail, M. J. et al., "Digital Microfluidic Method for Protein Extraction by Precipitation", Analytical Chemistry, 2009. 81: p. 330-335.

Jebrail, M. J. et al., "A digital microfluidic method for dried blood spot analysis", Lab on a Chip, 2011. 11: p. 3218-3224.

Jebrail, M. J. et al., "Synchronized Synthesis of Peptide-Based Macrocycles by Digital Microfluidics", Angewandte Chemie International Edition, 2010. 49: p. 8625-8629.

Kim, H. et al., "Automated Digital Microfluidic Sample Preparation for Next-Generation DNA Sequencing", Journal of the Association for Laboratory Automation, 2011. 16: p. 405-414.

Kim, H. et al., "A Microfluidic DNA Library Preparation Platform for Next-Generation Sequencing", PLoS ONE, 2013. 8(7):e68988 (9 pages).

Kim, H. et al., "Digital Microfluidic Hub for Automated Nucleic Acid Sample Preparation," 14th Int'l Conf. on Miniaturized Systems for Chemistry and Life Sciences, Groningen, The Netherlands, Oct. 3-7, 2010: p. 2035-2037.

Luk, V. N. et al., "Pluronic Additives: A Solution to Sticky Problems in Digital Microfluidics", Langmuir, 2008. 24: p. 6382-6389.

Malic, L. et al., "Integration and detection of biochemical assays in digital microfluidic LOC devices", Lab on a Chip, 2010. 10: p. 418-431.

Miller, E. M. et al., "A Digital Microfluidic Approach to Homogeneous Enzyme Assays", Analytical Chemistry, 2008. 80: p. 1614-1619.

Mousa, N. A. et al., "Droplet-Scale Estrogen Assays in Breast Tissue, Blood, and Serum", Science Translational Medicine, 2009. 1(1): 1ra2 (6 pages).

Ng, A. H. C. et al., "Digital Microfluidic Magnetic Separation for Particle-Based Immunoassays", Analytical Chemistry, 2012. 84: p. 8805-8812.

Paik, P. et al., "Electrowetting-based droplet mixers for microfluidic systems", Lab on a Chip, 2003. 3: p. 28-33.

Paik, P. et al., "Rapid droplet mixers for digital microfluidic systems," Lab on a Chip, 2003. 3: p. 253-259.

Pollack, M. G. et al. "Electrowetting-based actuation of liquid droplets for microfluidic applications", Applied Physics Letters, 2000. 77: p. 1725-1726.

Shah, G. J. et al., "Meniscus-Assisted High-Efficiency Magnetic Collection and Separation for EWOD Droplet Microfluidics", Journal of Microelectromechanical Systems, 2009. 18(2): p. 363-375.

Shih, S. C. C. et al., "A feedback control system for high-fidelity digital microfluidics", Lab on a Chip, 2011. 11: p. 535-540.

Thaitrong, N. et al., "Quality control of next-generation sequencing library through an integrative digital microfluidic platform", Electrophoresis, 2012. 33: p. 3506-3513.

Vergauwe, N. et al., "A versatile electrowetting-based digital microfluidic platform for quantitative homogeneous and heterogeneous bio-assays", Journal of Micromechanics and Microengineering, 2011. 21:054026 (11 pages).

Wheeler, A. R., "Chemistry—Putting Electrowetting to Work", Science, 2008. 322: p. 539-540.

\* cited by examiner

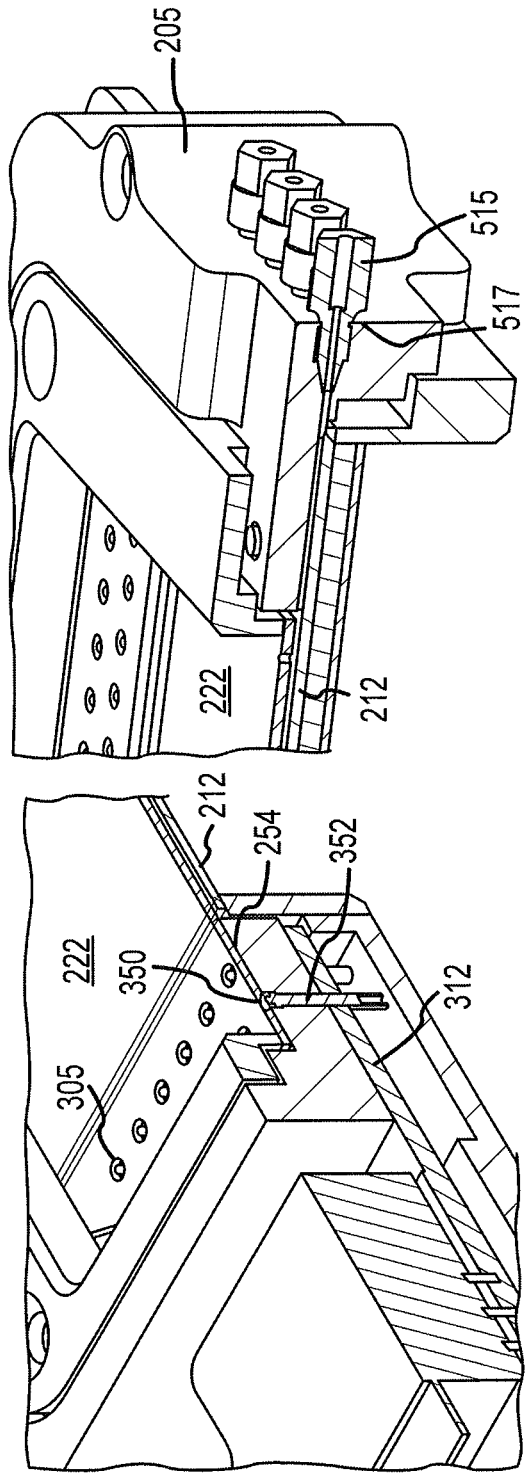

MICROFLUIDIC HUBS, SYSTEMS, AND METHODS FOR INTERFACE FLUIDIC MODULES

CROSS-REFERENCE TO RELATED APPLICATION(S)

This application claims the benefit of the earlier filing date of U.S. Provisional application 61/478,641 entitled "Digital microfluidic platform and method for interface," filed Apr. 25, 2011, which application is hereby incorporated by reference in its entirety for any purpose.

STATEMENT REGARDING RESEARCH & DEVELOPMENT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

TECHNICAL FIELD

Embodiments of the invention relate generally to microfluidic hubs, systems, and methods for interfacing fluidic modules. Examples of platforms for digital microfluidics are described that may facilitate integration of microfluidic systems.

BACKGROUND

Digital microfluidics generally refers to microfluidic technology using manipulation of fluid droplets. Droplets of unit size may be controlled, combined, reacted, analyzed, and/or stored. The fluid droplets may be moved by applying electric fields in proximity to the droplets. Accordingly, digital microfluidic devices may include a substrate patterned with electrodes and coated with a dielectric insulator and a hydrophobic film. By applying an electric field in an area adjacent a droplet, interfacial (e.g. electrowetting) and body forces are generated, which may attract the droplet into the region of higher field intensity, thus moving the droplet.

Generally, so-called 'open format' and 'closed format' digital microfluidic devices are available. FIGS. 1A-1B illustrate portions of an open and closed format digital microfluidic device, respectively.

As shown in FIG. 1A, an open format digital microfluidic device may include grounded traces, such as electrode 105 patterned on an electrode substrate 115. A droplet, such as the droplet 125 may be added to the device by using a pipette or eyedropper to place a desired amount of fluid on the device. A voltage may be applied, for example to another electrode 110, which may alter the contact angle between the droplet and substrate 115 and/or produce a localized electric field gradient, resulting in motion of the droplet 125 in the direction indicated by arrow 127 (e.g. toward the electrode 110). The droplet 125 will generally move until it is situated between the two electrodes shown. Typically, in open format devices, there may be a continuous ground electrode (e.g. a trace) running parallel to the stepping stone-like path (indicated schematically in FIG. 1A by a ground symbol shown above the droplet).

As shown in FIG. 1B, a closed format digital microfluidic device may include two substrates 150 and 155. A droplet, such as the droplet 164, may be placed on the substrate 150 prior to placing the lid 155 over the droplet 164. A spacer element, such as double-sided adhesive tape, a gasket, or a patterned layer, may be used to achieve a gap between the substrates 150 and 155 of about 10-1000 microns, bounding the placed droplet 164 on upper and lower surfaces. In some system, holes may be provided in the substrates 150 or 155 to provide reservoirs for fluid addition to the system. The substrate 155 (e.g. the lid) may include a ground plane electrode 160, while the substrate 150 may include an actuated electrode 162. When a voltage is applied to the electrode 162, an electric field may be generated between the electrode 162 and the electrode 160, exerting body forces on the droplet and altering the contact angle between the droplet and the surface of the substrate 150, 155, or both, and the droplet 164 may move toward the electrode 162 as shown in FIG. 1B. The space between the substrates 150 and 155 may be filled with immiscible fluid through which the droplet 164 may be moved, or may contain a gas or vacuum. During operation, under static conditions the digital microfluidic electrodes may be maintained in a grounded state. When droplet actuation (e.g. movement) is desired, an electrode nearest the droplet in the direction of desired motion may be activated (e.g. energized, a voltage being applied to the electrode). The resultant electric field may cause the droplet to move stepwise onto the energized pad as a result of electrowetting and/or body forces. To remove droplets, the lid is generally removed and the droplet aspirated.

BRIEF DESCRIPTION OF THE DRAWINGS

FIG. 4 is a schematic illustration of a close-up view of one registration surface and pogo pins making contact to electrodes the substrate 222 of using the fixture of FIGS. 2A and 2B.

FIG. 5 is a schematic illustration of a ferrule in a port defined by a frame in accordance with an embodiment of the present invention.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known circuits, control signals, timing protocols, and software operations have not been shown in detail in order to avoid unnecessarily obscuring the described embodiments of the invention.

The above-described existing digital microfluidic techniques may suffer from a variety of drawbacks. For example, the open format digital microfluidic devices, such as the portion shown in FIG. 1A, may impose limitations on the kind of droplet moving geometries that can be employed due to the need to always route both ground and actuated electrodes in close proximity on the same substrate. Overall, droplet actuation on an open format device may be somewhat more difficult to achieve consistently because electric field gradients and transients may be confined to a relatively small region at the base of the droplet in proximity to the gap between actuation and ground electrodes. A ground trace may also be routed on the substrate, further constraining the available substrate area in which to position actuatable electrodes. While the absence of a lid in an open format system may enable functionalities like environmental sampling of dust or aerosol particles, droplet evaporation also may become a more significant problem due to the comparatively large free surface area of the droplet.

Figure 1A:
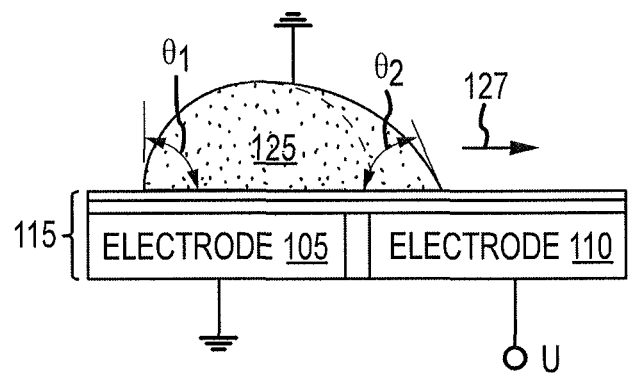
FIGS. 1A-1B illustrate portions of an open and closed format digital microfluidic device, respectively.
Figure 1B:
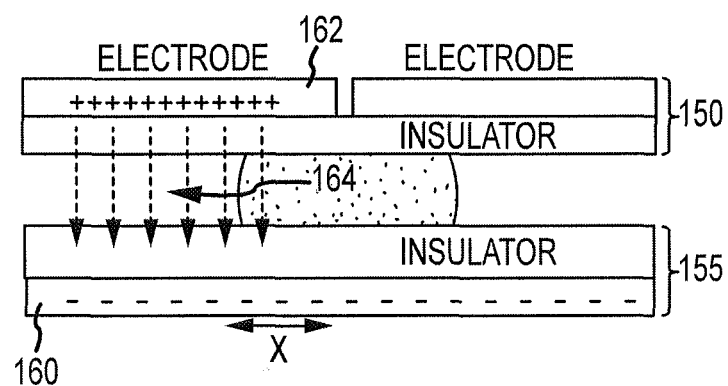

Closed format digital microfluidic devices, such as that shown in FIG. 1B, may be able to provide a greater degree of freedom in electrode positioning due to the presence of two substrates on which to provide electrodes. Closed form digital microfluidic devices may be able to eliminate the ground plane and pattern individually addressable electrodes on both top and bottom substrates. The closed format configuration therefore may enable more reliable droplet actuation by applying electric field transients and gradients across the full thickness of the droplet boundary, not just at its base. The closed format may also provide a significant degree of droplet confinement, limiting the surface area which is available for evaporation and allowing droplet-based devices to be largely indifferent to tilt angle or moderate acceleration. The closed format may also enable robust actuation of substantially smaller droplet volumes than those which can be handled in an open format. Finally, closed format devices may also provide a better controlled environment for working with multiphase systems (e.g. aqueous droplets surrounded by oil or other fluid).

However, closed format digital microfluidic devices may face challenges in fixturing the two substrates (e.g. substrates 150 and 155 of FIG. 1B) reliably and repeatably in close proximity to maintain a uniform and consistent gap in the tens to hundreds of microns range. Utilizing a spacer element (e.g. double-sided tape or a coverglass slip) may result in uncertainty in the actual gap height, as the spacer element thickness itself may be difficult to control in the tens to hundreds of micron range. Variations in gap height may adversely affect reliability and repeatability of droplet movement in a completed system. Moreover, physically placing the spacer may result in contamination, damage to the surfaces, and generally may limit how droplets may be introduced to the device.

Moreover, making robust electrical connections to the interior surfaces of such a closely spaced assembly and providing for the delivery of fluid droplets into the interstitial space between the two substrates (or removal of fluids from that space) may represent additional challenges.

Embodiments of the present invention may be used with either open or closed format digital microfluidic devices, or combinations of open and closed format digital microfluidic devices. Embodiments of the present invention may address individual or combinations of drawbacks of other techniques described herein. However, the drawbacks and advantages described herein are provided by way of example only, and are not intended to be limiting. It is to be understood that not all embodiments may address all described limitations or have all described advantages. Some embodiments may not address any described limitations or have any of the described advantages.

Embodiments of the present invention include microfluidic hubs, systems, and methods for interfacing fluidic modules. Examples of fixtures and methods for fixturing are described that may be advantageously used to implement microfluidic hubs. For example, example fixtures may be used to set a dimension between substrates and a droplet actuator provided to move a droplet within the space between substrates. For example, digital microfluidic technology may be used to implement the droplet actuator. The fixtures may be used for other types of microfluidic and non-microfluidic devices as well to set a distance between two substrates generally while providing a mechanism to access the space between them.

Example microfluidic hubs in accordance with the present invention may function to receive fluid from one or more fluidic modules (e.g. reservoirs, other microfluidic devices or systems, fluid sources) and manipulate droplets of the received fluid. The droplets may be manipulated using a droplet actuator positioned to act on droplets within the space between two surfaces. For example, digital microfluidic technology may be used to perform droplet operations such as, but not limited to, moving the droplets, mixing, aliquoting, or analyzing the droplets. Droplets may then be removed from the microfluidic hub and returned to the same fluidic module or delivered to another fluidic module. In this manner, microfluidic hubs and systems described herein may provide a fluidic router that may be used to interface disparate fluidic systems. Generally, fluid operations on the microfluidic hub are operations using discrete droplets. However, as described herein, example microfluidic hubs may integrate with continuous flow systems in addition to or instead of other discretized fluid systems.

Examples of droplet actuators that may be used include digital microfluidic technology (e.g. actuation electrodes and associated power that may utilize electrostatic and/or electrowetting forces). In other examples, droplet actuators may include fluid flow components designed to move droplets using fluid forces. For example, fluid flow directed at a droplet may be used to push the droplet from one position to another within the device. In an example of liquid droplets in an air ambient, this may be accomplished by directing a stream of air at a droplet. In an oil or liquid flooded device, articulation of immiscible droplets may likewise be implemented by inducing bulk flow in the surrounding medium. Similarly, suction forces may be used to move droplets. A droplet actuator may accordingly include a pressure source designed to apply a suction force (and/or a push) to a droplet it a desired direction. In other examples, gravitational and/or buoyancy forces may be used to move droplets. For example, a droplet actuator may include an actuator (e.g. a controller) to tilt a device relative to the vertical gravitational vector to move droplets in one or more axes. In liquid ambient devices, differences in density between two immiscible phases can yield buoyancy forces which similarly produce droplet motion in response to tilting or reorientation of the device. Mechanical vibration of one or both substrates may also provide a mechanism to drive droplets from one position to another within the device. Examples include the use of piezoelectric or surface acoustic wave devices as droplet actuators, the excitation of different resonant mode shapes to preferentially move droplets to node or antinode locations, or the use of high frequency vibrations generally to improve the reliability of droplet actuation by other mechanisms (e.g. rendering the droplet-surface interface "dynamic" to overcome static adhesion forces). Droplets including fluids with high magnetic permeability or suspensions of magnetic particles may be actuated using magnetic forces applied by permanent magnets, electromagnetic coils, or the like. Surface treatments or patterned features which impose droplet surface energy gradients or discontinuities may also provide a mechanism to actuate droplets from one position to another within the device (e.g. variable substrate-to-substrate spacing, converging/diverging lines on one or both substrates, graded surface roughness, patterned wicking structures, etc.). Imposed thermal gradients applied by thermal lensing, lasers, resistive heating, thermoelectrics, and the like may also provide a mechanism to transport a droplet within the device, either due to surface energy imbalances or as a result of evaporation from an actively heated portion of the device and recondensation in an actively cooled portion. Droplets may also be actuated using optical forces like those generated in optical tweezing and single-beam optical trap systems. Accordingly, droplet actuators may be implemented using any of these described mechanisms. Examples described below may highlight the use of digital microfluidic technology to manipulate (e.g. move) droplets within a space between two surfaces, however examples of the invention are not so limited and may be implemented using other droplet actuators instead of or in addition to digital microfluidic examples. Generally droplet actuators may be used that move droplets without a need to have the droplets constrained by physical channels between the surfaces. So, for example, a droplet actuator may be used to control droplet movement within an open space between two surfaces.

Figure 2A:
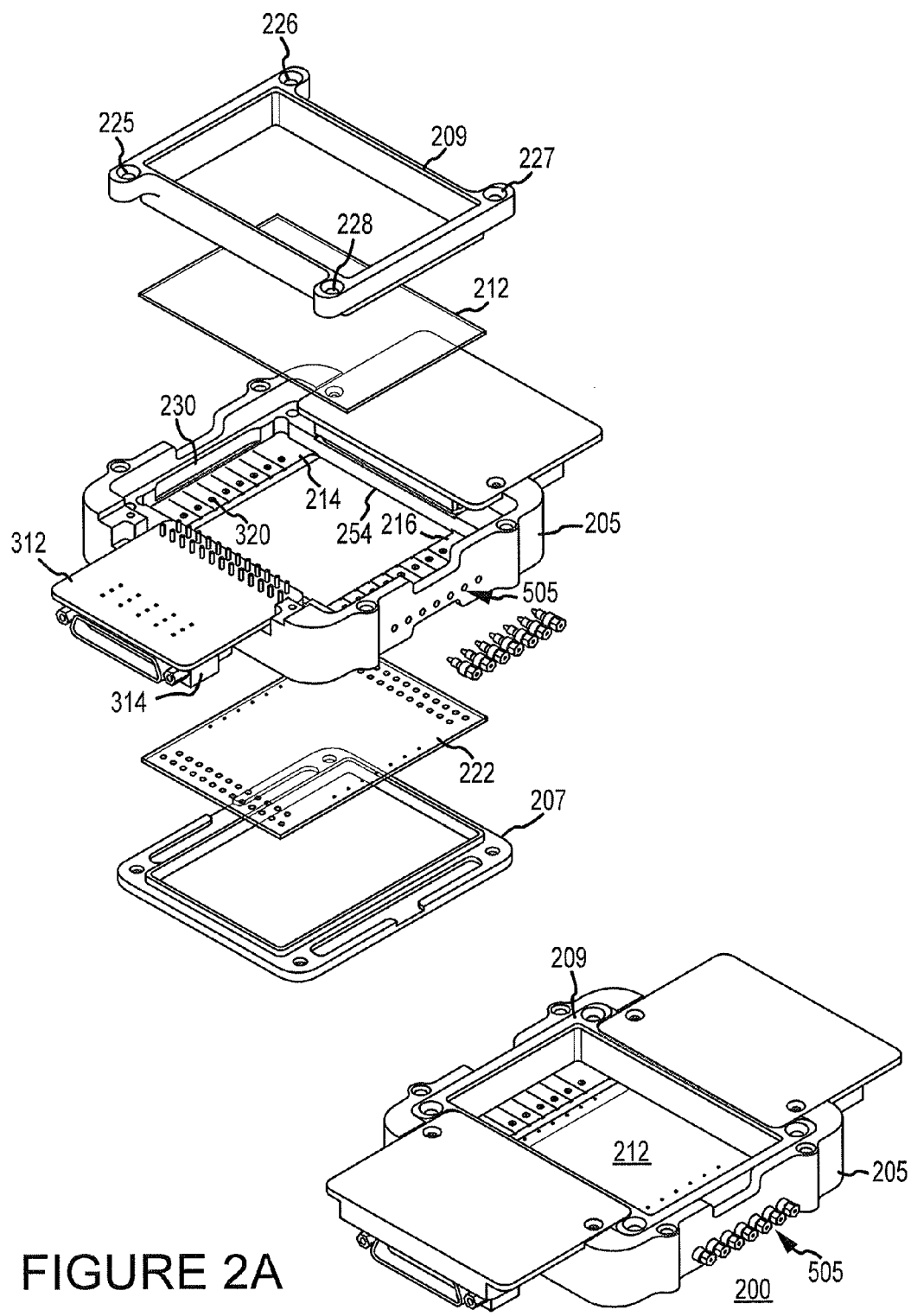
FIGS. 2A and 2B are schematic illustrations of a top and bottom view, respectively of an example fixture according to an embodiment of the present invention.
Figure 2B:
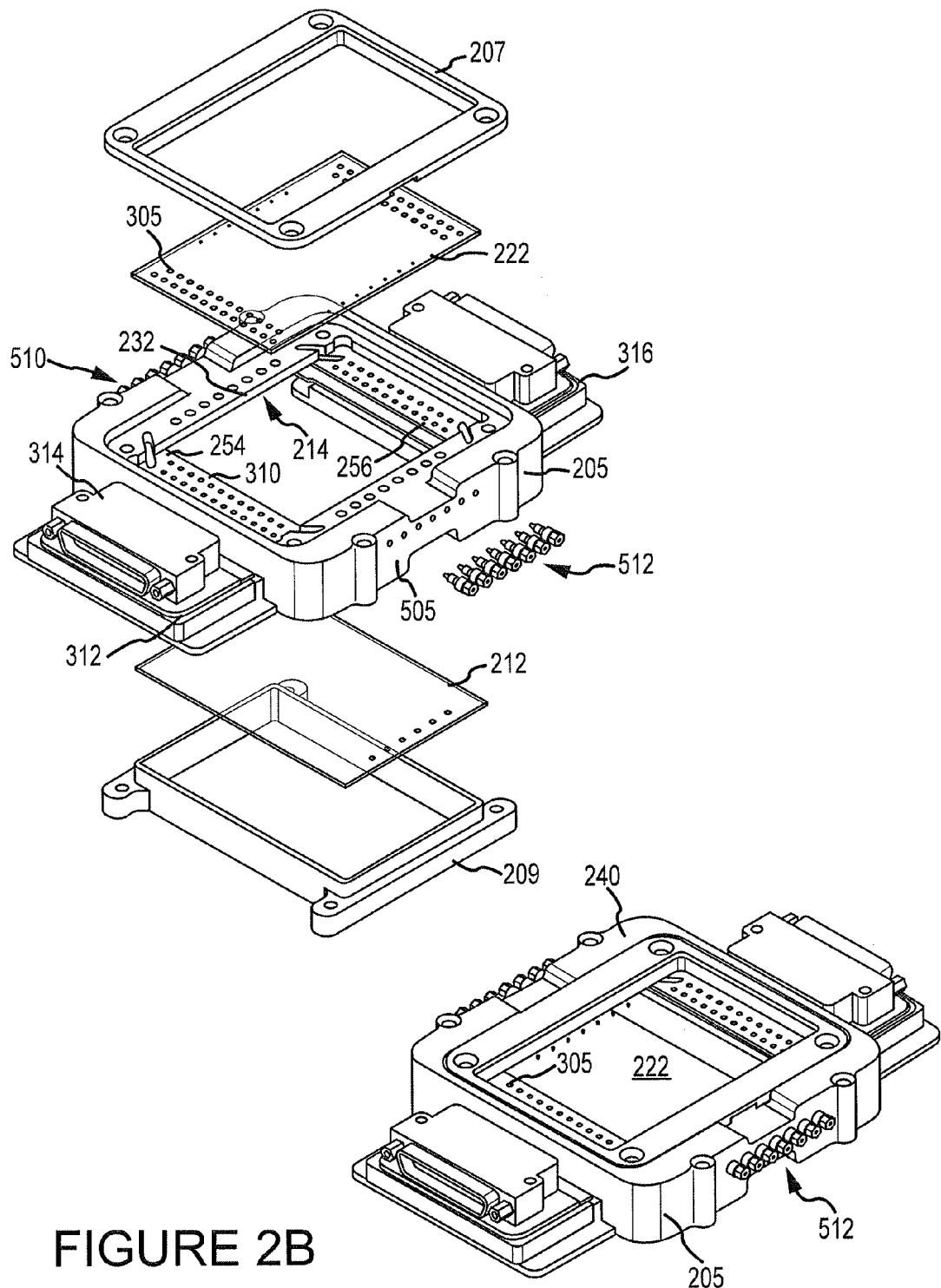

FIGS. 2A and 2B are schematic illustrations of a top and bottom view, respectively of an example fixture according to an embodiment of the present invention. FIG. 2A illustrates both an exploded and a compact bottom view of the fixture 200. The fixture 200 may be used in example microfluidic hubs in accordance with the present invention. The fixture 200 includes a compression frame including frame 205 and compression members 207 and 209. A substrate 212 may rest against surfaces 214 and 216 of the frame 205. A second substrate 222 may rest against different surface on an opposite side of the frame, described further with later reference to FIG. 2B. While the frame is shown with an open area that may be advantageous, for example, for optical access to the substrates 212 and 222, in some embodiments the frame may not define the open area, and for example, the surfaces 214 and 216 may coincide with the position of a solid or partially solid surface spanning all or part of the frame. The frame 205 accordingly may receive the substrate 222 and position the substrate 222 a predetermined distance from another surface, which may be a surface defined by the frame 205, or may be a surface of another substrate held by the frame 205, such as the substrate 212.

The compression members 209 and 207 may constrain movement of the substrates 212 and 222 by pressing against them, using fasteners which may be inserted, for example at locations 225-228. Any type of fasteners may generally be used, such as but not limited to bolts, clamps, clips, snaps, magnets, pins, screws, posts, glues, adhesives, or combinations thereof. The fasteners may extend through the compression members 209, 207, and frame 205, to hold the components together and the substrates 212 and 222 in place.

While the example embodiment described with reference to FIGS. 2A and 2B utilized discrete compression frame elements such as machine screws or other fasteners to hold each substrate against the registration surfaces of the frame, other methods of fixing or pressing substrates against these surfaces may also be used. Retention methods and elements including but not limited to magnets, spring clips, locking cams, frictional interference fits, adhesives, or combinations thereof may be used to maintain the position of the substrate against the registration frame, either with or without the presence of a separate compression frame. Compression frame elements may be implemented with a pivot or hinge at one end or articulated as part of a linkage or mechanism to allow them to be controllably moved into position before being locked in place. Other embodiments of the invention may include provisions for continuously or discretely varying the gap spacing between opposed registration surfaces, and therefore the spacing between substrates, which may facilitate accommodating droplets of different volumes.

Referring to FIG. 2B, a bottom-up view of the compression members 207 and 209 and frame 205 is shown. The substrate 222 may rest against surfaces 254 and 256 of the frame 205. Note that the orientation of the substrate 222 is 90 degrees from the orientation of the substrate 212. By utilizing substrates having different orientations, the assembled device may have overlapping and non-overlapping portions of the substrates 222 and 212. For example, the substrates 212 and 222 overlap in an open region of the frame 205. However, the substrates 212 and 222 do not overlap where the substrates are resting on respective surfaces of the frame 205. Accordingly, no one dimension of any portion of the frame 205 may act as a spacer to directly set the gap between the substrates 212 and 222. Instead, a distance between planes defined by different surfaces of the frame may set the gap distance between the substrates 212 and 222. A predetermined distance between facing surfaces, such as the surfaces of the substrates 212 and 222, may be determined by a distance in the normal (e.g. out-of-plane) direction between the plane defined by surfaces 214 and 216 and that defined by the surfaces 254 and 256.

The predetermined distance between the surfaces maintained by the fixture (e.g. the substrate-to-substrate spacing or gap between the surfaces) may be between 10 and 100 microns in some examples, between 10 and 50 microns in some examples, between 10 and 20 microns in some examples, between 10 and 500 microns in some examples, between 100 and 200 microns in some examples, between 100 and 500 microns in some examples. In some examples, gaps of up to several millimeters may be used. In one example, a 185 micron gap may be used. Generally, the substrate-to-substrate spacing may be in the range of tens of microns to ten millimeters. The spacing may vary in accordance with the aspect ratio of droplets desired for use in a microfluidic hub including the fixture—generally the aspect ratio of the droplets will be determined in part by the gap height vs. the electrode width used to move the droplets. In one example, for 2.5 mm wide electrodes, a gap of between 185 microns and 400 microns may be used. In some examples larger electrodes may be used and larger gap spacing. Voltage supplied to the electrodes may also vary accordingly to achieve movement of the droplet.

For example, the surfaces 214 and 216 of FIG. 1A may define a plane that the substrate 212 may be placed on. The surfaces 254 and 256 of FIG. 2B may define another plane that the substrate 222 may be placed on. The distance between the planes defined by the surfaces 214 and 216 and the plane defined by the surfaces 254 and 256 may define a gap distance between the two substrates 212 and 222. In this manner, a thickness of portions of the frame 205 defining the surfaces 214 and 216 may be unrelated to the gap distance between the two substrates. Similarly, thicknesses of portions of the frame 205 defining the surfaces 254 and 256 may be unrelated to the gap distance between the two substrates. The frame 205 may be constructed using thicknesses suitable for machining or other fabrication techniques that may be readily reproducible and reliable.

In other examples, only one substrate and a frame may be used, and two substrates may not be required. For example, the frame itself may furnish one or more registration surfaces against which one substrate is held, maintaining its position relative to a second surface, which is provided by the frame itself. The second surface provided by the frame may be made of or coated with conductive material to form a ground plane electrode, or the surface can be patterned with individually addressable electrodes. The second surface may furthermore be coated with electrically insulating layers and/or hydrophobic layers, allowing it—in conjunction with a substrate installed against the registration surfaces of the frame—to form a closed format digital microfluidic device. As in the example shown in FIGS. 2A and 2B, ports in the frame provide the ability to precisely fix capillaries and/or other elements in position between the frame-integral surface and the substrate.

In this manner, examples of frames according to the present invention may define a space between two surfaces (e.g. two substrates or one substrate a surface provided by the frame). A space may then be defined between the two surfaces, and a droplet actuator may be provided to manipulate (e.g. move) droplets within the space between the two surfaces. Controller movement or other manipulations may be achieved without a need to bound the fluid droplet on additional sides (e.g. through the use of physical channels).

The frame 205 and compression members 207 and 209 may be made of a same or of different materials. Generally any materials suitable for machining or fabricating into the desired structures may be used—including metals or polymers. Substantially any machining or fabrication techniques may be used, including CNC machining in some examples. In one example, the frame 205 may be made of a machined polymer and the compression members 207 and 209 may be made of aluminum. Other materials may be used in other examples.

The frame 205 may be a rigid and dimensionally stable structure. The frame 205 may define a central open area, as shown in FIGS. 2A and 2B which may enable optical access to the substrates from both top and bottom. In some examples, the area may not be open or may provide optical access to only one substrate. Two-sided optical access may be advantageous in examples where electrodes and structures patterned on the substrates 212, 222 are transparent (e.g. conductive indium tin oxide used to form the electrodes).

The frame 205 may be machined or fabricated in such a way that its upper and lower surfaces each define a depression, e.g. a pocket, sized to accommodate a substrate. For example, pockets 230 and 232 are shown in FIGS. 2A and 2B. Lateral alignment of the substrates may be provided to within some moderate tolerance by the walls of the pocket, while the position of the substrates in the normal direction may be constrained by two pairs of registration surfaces, e.g. the surfaces 214, 216 in FIG. 2A and the surfaces 254, 256 in FIG. 2B. The pair 214 and 216 are set within the pocket 230, defining a bottom of the pocket. The other pair 254 and 256 are within the pocket 232. Each set of registration surfaces may provide a flat and mechanically robust planar surface against which non-overlapped portions of a surface of the substrates may rest. The substrates 212, 222 may be held against the registration surfaces 214, 216, 254, 256 of the frame 205 by frame members 207, 209 which may be bolted, clamped, snapped, glued, adhered, or magnetically held in position (or combinations of those fasteners) against the outside surface of the substrates. Compression frame members 207 and 209 may also be positioned, engaged, or disengaged using a hinge or mechanical linkage in conjunction with fasteners as noted above. Relative to the use of spacers between substrates to set a gap distance between them, the overall design of the fixture 200 may not require fabrication of a spacer element having a thickness equal to the gap thickness. While the offset between registration surfaces should be carefully controlled when manufacturing the frame 205, no thin member defines the substrate-to-substrate offset (e.g. gap distance). Instead, the predetermined distance between surfaces may be set by the frame 205 using a distance between planes defined by registration surfaces of the frame, as has been described above.

The substrates 212 and 222 may be formed of the same or different materials. In some examples, the substrates 212 and 222 may be substrates suitable for use in digital microfluidic technology. The substrates may be transparent or partially transparent, and may for example be quartz, glass, polymer, or ceramic. In some examples, one or more of the substrates may be rigid and self-supporting across an opening defined by the frame. In some examples, a thin-film may be used, and may for example be stretched tight across an opening defined by the frame. The substrates may include electrodes and/or pads, which may be made of any suitable conductive material, including thin metal films or transparent conductive materials such as indium tin oxide (ITO). Other substrates may also be used including metal or semiconductor substrates. Although shown as rectangular in FIGS. 2A and 2B the substrates 212 and 222 may have other dimensions in other examples. In one example, the substrates may have dimensions of 50 mm×75 mm×1 mm and may be overlapped to yield a 50 mm×50 mm overlap area.

The substrates 212 and 222 may support patterned or blanket electrodes. The patterned electrodes may be used to move droplets in accordance with digital microfluidic technology. In other examples, the patterned electrodes may be used to provide voltages, electric fields, heating, thermometry, or otherwise provide functionality to a microfluidic system. In some examples, one of the substrates 212 or 222 may have a ground electrode while the other of the substrates may have patterned electrodes that may be addressed to apply voltages to a particular location. The ground electrode may also be patterned, or it may be a single electrode covering the entire substrate.

The substrates 212 and 222 may include an insulating material covering all or portions of the electrodes. Any of a variety of insulating material may be used, including but not limited to, oxides, nitrides, or polymers. Example insulating materials include, but are not limited to, parylene, SU-8, silicon nitride, silicon dioxide, or combinations thereof. The insulating material may be provided on the substrates using any suitable fabrication technique, including oxide growth, material deposition, or the like. The substrates may also support a hydrophobic material. Example hydrophobic materials include, but are not limited to, Teflon, FluroPel V-polymer, CYTOP, or combinations thereof.

In the examples shown in FIGS. 2A and 2B, the substrates 212 and 222 are glass substrates of identical size (e.g. 50×75 mm, <1 mm thick). While shown as a same size in FIGS. 2A and 2B, the substrates 212 and 222 may be of different sizes. In some examples, one substrate may be smaller than the other to form, for example a partially-open and partially-closed digital microfluidic configuration. Other sizes and thickness of course may be used. The substrates 212 and 222 may be positioned in close proximity with their electrode or functional surfaces parallel and face to face. The substrate 222 is rotated at 90 degrees and positioned symmetrically relative to the substrate 212 creating a central 50×50 mm overlapping region which may define the functional portion of the resulting device, which may be a closed format digital microfluidic device. This example arrangement leaves 12.5 mm at the ends of each substrate that is not facing or overlapping the other substrate and may therefore be accessible for making electrical connections to the surface of each substrate, as will be described further below. In other examples, similar configurations may be used resulting in both overlapping and non-overlapping areas, which may enable electrical or fluidic access to a portion of the inner surface of each substrate while the overlapping areas may define the gap space advantageous for microfluidic droplet manipulating functionality, e.g. digital microfluidics.

While the example embodiment shown in FIGS. 2A and 2B illustrates two substantially planar substrates fixed parallel to one another, non-planar substrates may also be positioned in proximity in other examples to allow droplet actuation between them. Non-uniform substrate-to-substrate spacing and substrates with defined topography may also be advantageous in some embodiments to allow handling of smaller droplets in one portion of the device and larger droplets in another. The example embodiment of FIGS. 2A and 2B may also amenable to use in an open format (e.g. single substrate) or a hybrid open/closed device in which the lid substrate covers only a portion of the active device area.

In FIGS. 2A and 2B, the substrates 212 and 222 are not centered in the frame 205 in the normal direction. Looking at the collapsed views, the substrates are positioned closer to a bottom surface 240 of the frame 205. If the fixture 200 is mounted on an inverted microscope stage in an appropriate orientation, the substrates 212 and 222 will be in closer proximity to the stage and therefore the focal plane of the microscope. In this case, long working distance objectives may not be necessary and higher numerical aperture objectives may be used. In general, the frame 205 and frame members 207 and 209 may be designed to have a relatively low profile in the normal direction to make microscopy advantageous from either the top or bottom of the platform (regardless of orientation) and as simple and flexible as possible. In examples where microscopy is not used however, such concerns may not be present at the substrates may be positioned at any location along the normal thickness of the frame 205.

Generally, fixtures in accordance with embodiments of the present invention may utilize transparent (which term is used to also include partially transparent) materials such that optical access may be had to one or both sides of the substrates forming an active area of the device. Examples of optical analysis techniques that may be used to view and/or analyze fluids within substrates described herein include, but are not limited to, transmission and epifluorescence microscopy, optical absorbance, laser-induced fluorescence, and Raman spectroscopy.

Accordingly, embodiments of the present invention provide fixtures, such as the fixture 200 of FIGS. 2A and 2B, that may include a frame that may position a substrate a predetermined distance from another surface. In some examples, the frame may hold two substrates spaced apart from one another by a predetermined distance. The fixtures may provide a first surface that receives a first substrate, and a second surface that receives a second substrate. The substrates may contact the respective surfaces in areas outside of the regions in which the substrates overlap. In this manner, the distance between the substrates may be defined by the distance between the first and second surfaces, which may not be represented by a thickness of any portion of the frame. In this manner, an entire area of an overlapping region of the substrates may be available for use in droplet actuation, e.g. using digital microfluidics. Further, embodiments of the fixtures may avoid complications associated with positioning spacers against the active surfaces of those substrates.

Electrical and fluidic connections to microfluidic devices may be made in any of a variety of ways. Any suitable techniques may be used to provide electrical and fluidic connections to the substrates 212 and 222 of FIGS. 2A and 2B in accordance with embodiments of the present invention. Some examples of electrical and fluidic connections are described further herein, some of which may be facilitated by use of fixtures in accordance with embodiments of the present invention that define substrate-to-substrate spacing using different surface of the fixtures. However, examples of electrical and fluidic connections described herein may also be used with devices having spacing defined more conventionally, e.g. using a spacer element having a thickness equal to the substrate-to-substrate spacing.

Although electrical connections are described herein with reference to the fixture 200 of FIGS. 2A and 2B, examples of the electrical and fluidic connections described herein may be used with other fixtures that may provide substrate spacing in different ways. Referring back to FIG. 2B, the substrate 222 may have patterned electrodes. The electrodes may be connected to pads—pad 305, for example. The pads (which may themselves be electrodes) are generally used to make electrical connection off the substrate 222, as will be described further below. The pads may be connected by conductive traces to electrodes that may be positioned anywhere on the substrate 222. Each pad may be connected to 0, 1, 2, or more electrodes. The pads may be provided on an area of the substrate 222 that may not overlap the substrate 212 when the compression frame is fastened together. Instead, the pads may be provided on an area or areas of the substrate 222 that contacts the registration surfaces 254 and 256. Accordingly, the registration surfaces 254 and 256 may be used to make electrical connection to the substrate and any electrodes on the substrate. In an analogous manner, the registration surfaces 214 and 216 may be used to make electrical connections to the substrate 212, which may also include pads and electrodes, or may be a single conductive ground electrode.

Accordingly, conductive contacts may be provided on the registration surfaces 254, 256, 214, and 216. In other examples, as shown in FIGS. 2A and 2B, the frame may define voids (e.g. holes, recesses) opening into the registration surface—hole 310 for example in the registration surface 254. Conductive connectors (e.g. pogo pins or plating) may then be placed in the voids to make connection between the substrate and a printed circuit board or other control, e.g. printed circuit board 312 of FIGS. 2A and 2B. The printed circuit board may be connected to a standard electrical connector, e.g. a serial connector 314. Another printed circuit board 316 may be provided for, a plurality of circuit boards may be provided for, or only one printed circuit board may be used and all pads may be connected to that single printed circuit board, or conductive traces may connect selected ones of the pads together and to the printed circuit board. The printed circuit board itself may not be present in some examples, and other mechanisms of connecting external electrical equipment to conductive material in the holes of the frame may be provided.

The fixture 200 provides 46 independent pogo pin contacts to the substrate 222 and sixteen, typically jumpered together, to the substrate 212. The contacts to the substrate 212 may primarily provide redundancy in establishing an electrical ground reference, in other examples, the 16 pins may not be connected together, allowing their use to independently actuate electrodes on the substrate 212. Accordingly, examples of fixtures in accordance with the present invention may provide actuation of independently addressed pads (and therefore address individual electrodes or groups of electrodes) on both top and bottom substrates, which may allow for "cross-reference" type row-and-column addressable electrode schemes and other advanced functionalities spanning both substrates. For example, in some examples, electrodes on both substrates 212 and 222 may be addressable, and electric fields may be applied to fluids between the substrates in manner dictated by the electrodes selected on each substrate.

Figure 3:
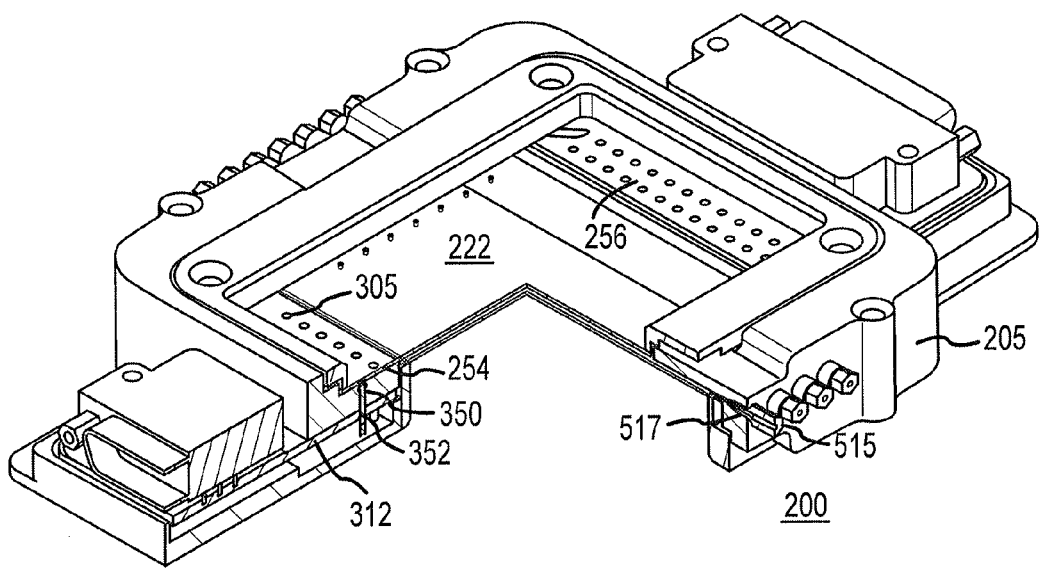
FIG. 3 is a schematic illustration of a quarter section bottom view of the fixture 200 of FIGS. 2A and 2B.

To further illustrate examples of electrical connections in accordance with embodiments of the present invention, FIG. 3 is a schematic illustration of a quarter section bottom view of the fixture 200 of FIGS. 2A and 2B. A cross-section of a hole 350 defined by the frame 205 may be seen, in which is disposed a compliant spring contact 352 (e.g. pogo pin). A similar hole may be defined in frame 205 corresponding to each pad on the substrate 222 and may have a complaint spring contact disposed therein. The compliant spring contact 352 may be at rest in the frame 205 above the registration surfaces (e.g. surface 254) until the substrate 222 is pressed flush against the registration surface by its compression member, at which point the spring contacts may be compressed against contact pads patterned on the substrate 222, providing adequate contact force for robust electrical connectivity. Similar compliant spring contacts may be provided associated with the registration surface 256. The non-compliant end of each spring contact (or selected spring contacts) may then be connected to a printed circuit board 312, or may be connected to the control electronics by conventional mechanisms. FIG. 4 is a schematic illustration of a close-up view of one registration surface and pogo pins making contact to pads on the substrate 222 of using the fixture of FIGS. 2A and 2B. The pogo pin 352 is shown pressed against the substrate 222 through the hole 350 in the frame 205. The pogo pin 352 contacts the printed circuit board 312 that may be connected to an externally-accessible electrical connector.

To assemble the fixture 200, a substrate, e.g. substrate 222, may be placed face-down into the pocket 232 of the frame 205 as shown in FIG. 2B, registering in position laterally due to the dimensions of the pocket 232 and resting atop an array of electrical contacts (e.g. extended pogo pin spring contacts). Any number of electrical contacts (e.g. pogo pin spring contacts) may be used, with 46 shown in FIG. 2B. The compression member 207 may then be positioned above the substrate 222 and tightened in place with fasteners (e.g. four corner screws), which may compress any spring contacts and press the substrate 222 flat against the registration surfaces 254, 256 on either end of the frame 205. The frame 205 may then be inverted as in FIG. 2A, and the sequence of operations repeated for the second substrate 212. The substrate 212 may be positioned face down in the pocket 230 atop the electrical contacts, including contact 320. Any number of contacts may be provided for the substrate 212, with 16 shown in FIG. 2A. The substrate 212 is provided with fewer electrical contacts in the example of FIGS. 2A and 2B because the electrical contacts are used to ground the substrate 212 which in the example of FIG. 2A serves as a ground electrode, and may not include addressable electrodes. The compression member 209 may be positioned and fastened in place (e.g. with four screws) until the substrate 212 is situated flush against the registration surfaces 214 and 216. In this manner, robust electrical connection may be made to both substrates 212 and 222 as the substrates are held at a small, precisely defined gap ranging from tens to hundreds of microns, as set by the frame.

Embodiments of the present invention include a feature to access the interior of the gap space such as for fluid connection systems and methods for connecting or probing fluids into a gap space of the microfluidic device. Examples will be described with reference to the fixture 200 shown in FIGS. 2A and 2B. However, it is to be understood that the examples of fluid connection technology described herein may be used with or without other aspects of the fixture 200 described herein, such as the surface spacing and electrical interconnection technologies described.

Referring back to FIG. 2B, the frame 205 may be machined or fabricated with access ports 505, 510 along one or more sides. Access ports 505, 510 are shown on two sides in FIG. 2B, however, ports may be provided on one, two, three, or four sides of the frame 205. Any number of sides, and any amount of ports on each side, may be used. The access ports may be sized to allow fluid conduits (e.g. capillary tubes) to be inserted into the access ports. Other-cross sectional openings may be used to implement the access ports, such as slits in some examples While fluid conduit (e.g. capillary) insertion into the access ports is described further herein, in other examples, other fluid or gas conduits may be used, including conductive conduits.

Ports in the frame generally provide the ability to introduce and precisely position a variety of objects (e.g. interface elements) in the space between the two substrates/surfaces. Typically having high aspect ratios (length/width) these interface elements can be fluidic, thermal, electrical/electromagnetic, mechanical, or optical in nature. Examples of fluidic interface elements include fluid conduits such as capillaries, tubes, needles, multi-pore fibers, microchannels fabricated in thing chips, pores formed in laminated structures, wicking structures, and porous elements like sintered monoliths. Examples of thermal interface elements include thermocouples, heaters, thermoelectric heater/cooler elements, thermopiles, resistive temperature detectors, incandescent filaments, and thermally conductive wires, rods, or needles generally, which may be used to conduct heat to or from a droplet brought into contact with them. Electrical or electromagnetic interface elements include wires and electrodes as well as capacitive, resistive, and inductive components, transistors, coils, magnets, electromagnets, solenoids, and the like. Mechanical interface elements include piezoelectric rods/stacks, ultrasonic transducers, articulated probe tips, rotary shafts/armatures, and micromanipulators. Optical interface elements include optical fibers, waveguides, diodes, photodiodes, phototransistors, Fabry-Perot interferometers, and fiber-based surface plasmon resonance or surface enhanced Raman spectroscopy probes. Interface elements may also have non-cylindrical cross-sections. For instance, a wide, thin laminated tape with embedded tips or fashioned channels that taper down to tips can be positioned in the space between the two substrates/surfaces. Ribbon fluid elements have the advantage of easy registration of multiple interfaces in a multiplex fashion. The objects positioned in one or more of the ports need not be solely for the purpose of carrying fluids, objects for sensing or analyzing may be inserted into the access ports instead of or in addition to fluid conduits to provide additional functionality to the fixtures described herein. Combinations of these interface elements may be positioned in various ports of the devices to provide desired functionality.

The fluid conduits (e.g. capillary tubes) may extend through the ports 505, 510 into the space between the two substrates 212, 222 (or a substrate and a surface in other examples). The fluid conduits may be held in place by ferrules, tube fittings (e.g. CapTite ferrules 512), or adhesives. Guide holes may position the fluid conduits (e.g. capillaries) parallel to and equidistant from the top and bottom substrates 212 and 222, and the axial position of the capillary end may be readily adjusted by sliding the tube in or out before tightening it in place with the swaging ferrule or tube fitting. Other methods may be used to fixture a fluid conduit in position, including but not limited to clamping, crimping, gluing, or friction fits (e.g. heat-shrinking). In other embodiments, the access ports may position fluid conduits or other elements parallel to but not equidistant between the top and bottom substrates 212 and 222. In some examples, objects inserted into an access port may extend through a fixture and exit the fixture at another access port. This may be advantageous for objects such as wires or optical waveguides, but may also be used for fluid conduits.

The fluid conduits may be used to introduce fluids to the space between two surfaces, remove fluids from the space between two surfaces, or both. Fluid may be moved toward a fluid conduit, away from a fluid conduit, or between a fluid conduit, using droplet actuators, including microfluidic technology described herein.

FIG. 3 provides a cross-sectional view of a ferrule 515 positioned in a port 517 of the frame 205. FIG. 5 is a schematic illustration of a ferrule in a port defined by a frame in accordance with an embodiment of the present invention. As can be seen in FIG. 5, a capillary may be inserted into the ferrule 515, and may extend through the port in the frame 205 into the gap between the substrates 222 and 212 for controlled delivery of fluid at a specific location. The substrate-to-substrate distance may be sufficiently large to accommodate the outer diameter of the capillary tube. In some examples, the capillary tubes may be on the order of 90 microns, up to 360 microns in some examples. In one example, 170 micron diameter capillaries may be used. Accordingly, the geometry of the frame 205 may be provided such that a substrate-to-substrate gap is defined sufficiently large to accommodate the capillary, fiber optic, wire, or other object used.

Figure 6:
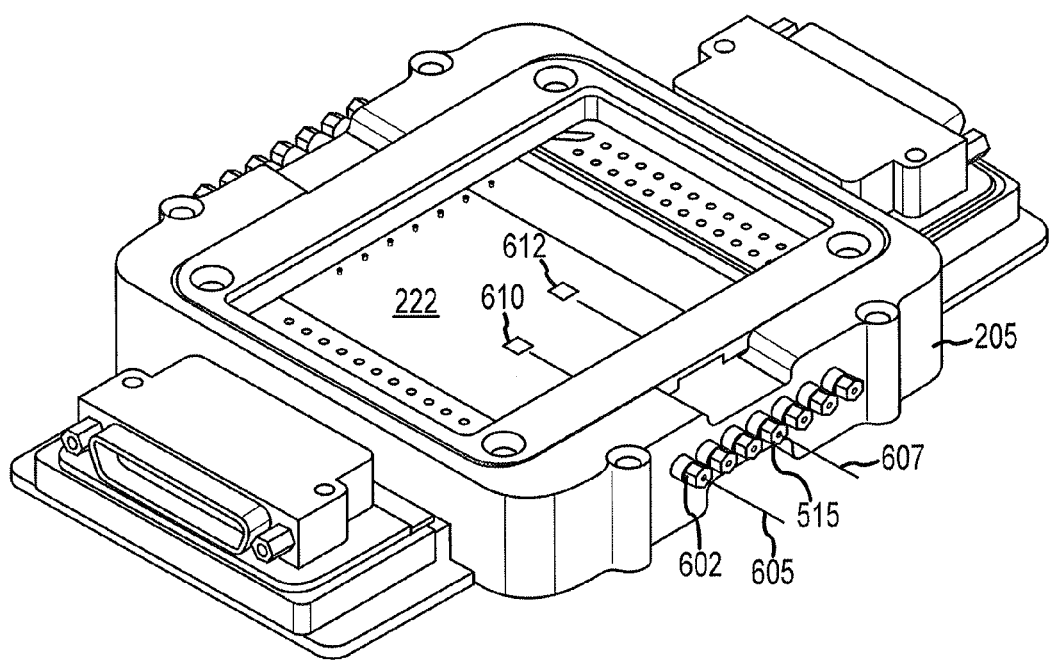
FIG. 6 is a schematic illustration of the fixture of FIG. 2A showing capillaries inserted into the fixture.

FIG. 6 is a schematic illustration of the fixture of FIG. 2A showing capillaries inserted into the fixture. Recall the substrate 222 may include a variety of electrodes that may be used to manipulate fluid droplets in examples where digital microfluidic technology is used as a droplet actuator. Example manipulations that may occur using digital microfluidic technology include droplet operations such as, but not limited to, merging, splitting, mixing, and aliquotting. Electrodes 610 and 612 are shown schematically in FIG. 6, but generally any number and arrangement of electrodes may be provided. The electrodes 610 and 612 may be connected to one or more of the pads described above using conductive traces on the substrate to allow for activation of the electrodes 610 and 612 from external power sources. In digital microfluidic technology, some electrodes may serve as reservoirs. For example, fluid may be collected or introduced proximate to a particular electrode serving as a reservoir. Fluid droplets may then be moved or divided from the reservoir array to accomplish desired functions. In some examples, capillaries may be positioned proximate particular electrodes to allow for introduction of fluid proximate those electrodes. For example, the capillary 605 may be provided such that the end of the capillary 605 is proximate the electrode 610, as shown. As will be described further below, the capillary tips may generally be positioned at an area near an electrode (e.g. adjacent or proximal to an electrode). Recall the electrode may generally be separated from the space between the surfaces, and therefore the fluid conduit, by a layer of hydrophobic material. Fluid introduced through capillary 605 may be controlled using the electrode 610 and electrodes proximate the electrode 610. Similarly, the capillary 607 may be positioned such that the capillary is proximate the electrode 612 so fluid introduced by the capillary 607 may be controlled using the electrode 612 and electrodes proximate the electrode 612.

Fluid conduits (e.g. capillaries) may be reliably positioned proximate particular electrodes in embodiments of the present invention. For example, the capillary 605, 607 may be placed into the ferrule 602, 515 and inserted into the gap between the substrates 222 and 212 until the capillary reaches a location proximate the electrode 610, 612. When the capillary is in position, the ferrule may hold the capillary in the same position. In some examples, capillaries may be fixed in position on a semi-permanent basis. Substrates may even be installed or removed in some examples from either side of the frame without disturbing the capillaries 605 and 607. In this manner, disassembly and reassembly of the fixture for experimental iterations or cleaning may effectively be a "plug-and-play" operation. The capillaries may be used to introduce fluid to the space between substrates, remove fluid from the space between substrates, or combinations thereof. While examples described herein may describe fluid introduction, it is to be understood that the same or analogous examples may also provide fluid removal. In some examples, repeated introduction and removal of various amounts of fluid may occur to move fluid into and/or off of a microfluidic hub as described herein.

In some examples, the capillaries inserted between the substrates may be hydrophobically-clad capillaries with hydrophilic inner surfaces. For example, capillaries used in examples of the present invention may have a hydrophobic surface treatment applied to the outer surfaces of the capillary (e.g. the tip and lateral walls) while the inner surface may be treated to make it hydrophilic or a native hydrophilic quality of the interior material (e.g. glass) may be preserved. This combination of hydrophilic and hydrophobic surfaces may facilitate effective transfer of droplets to and from the region between the electrodes. Suitable capillaries include, but are not limited to, glass or fused silica capillaries that may be coated or pre-coated with Teflon or another hydrophobic material. Before coating, the capillaries may be cleaved to yield a flat fracture surface normal to the axis of the capillary. Wetting the hydrophilic interior of the capillary prior to coating may prevent the hydrophobic coating from affecting the interior naturally hydrophilic surfaces of the glass capillary. In some examples, the capillary shaft may be coated with a hydrophobic coating discouraging wicking along the length of the capillary. Ends of a fluid conduit, such as a capillary, may be fashioned into a tip or other geometry in some examples to facilitate removing and introducing the capillary into a space between two surfaces.

The ports in the frame 205, e.g. the ports 505 and 510 of FIG. 2A, may be positioned to cause the capillaries to be disposed equidistant between the two substrates 212 and 222. Positioning the capillary equidistant between the substrates may be advantageous for droplet transfer operations. In digital microfluidic embodiments, the substrates 212 and 222 may be hydrophobic. Accordingly, droplets in the closed-format device may exhibit a convex cross-section, bulging furthest outward at the mid-plane between the substrates. As a result, well-centered in-plane capillaries may advantageously engage the highest radius of curvature portion of the droplet, contributing to the ease of complete droplet transfer onto the capillary.

During operation, fluid sources may be connected to the fluid conduits inserted between the substrates, e.g. the capillaries 605 and 607 in FIG. 6. Generally, any fluid sources may be used including reservoirs. In some examples, described further below, other microfluidic modules may have a fluidic input or output coupled to one or more of the capillaries (e.g. capillary 605 and/or 607) such that fluids may be moved between different fluidic modules using the fixture 200. When fluid is introduced to the capillaries, e.g. by pressure-driven or other flow mechanisms, a droplet may grow suspended on the capillary tip for some time until it reaches a critical size. The central positioning of example capillaries may in some examples facilitate the growth of a droplet. Once a droplet reaches a sufficient size, the droplet may snap into contact with the substrates (e.g. the substrates 222 and 212) at some distance away from where the annular surface of the capillary is in close proximity to the surface, allowing the droplet to be moved or otherwise manipulated using the electrodes.

For example, a microfluidic hub including at least an example frame of a fixture described herein, a fluid conduit, and a droplet actuator may be implemented using techniques described herein. The microfluidic hub may allow fluid to be introduced into the space between two surfaces using a fluid conduit positioned in an access port of an example frame described herein. A droplet of fluid may be introduced into the space between the two surfaces and any number of droplet operations may occur using the droplet actuator, including moving the droplet in a desired direction (e.g. along an electrode path). Suitable electrode layouts for use with digital microfluidic technology are described further below. Droplets may be removed from the microfluidic hub using the same or a different fluid conduit inserted through the frame. In this manner, the microfluidic hub may serve as an interface between multiple fluid modules.

Figure 7:
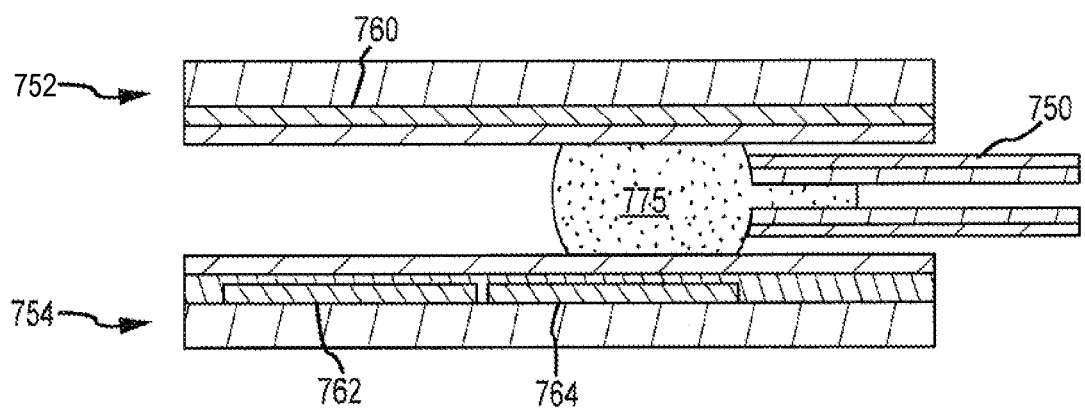
FIG. 7 is a schematic illustration of a cross-section of a capillary and droplet positioned between two substrates in accordance with embodiments of the present invention.

FIG. 7 is a schematic illustration of a cross-section of a capillary and droplet positioned between two substrates in accordance with embodiments of the present invention. A capillary 750 is shown, which may be used to implement the capillary 605 or 607 of FIG. 6. The capillary 750 may be a Teflon-coated glass capillary in some examples. The capillary 750 is positioned between two substrates 752 and 754. The substrates 752 and 754 may be used, for example, to implement the substrates 212 and 222 described above and shown, for example in FIGS. 2A-2B. The substrates 750 and 754 may be implemented as glass substrates. The substrate 750 has an electrode 760, which may be a ground plane electrode. The substrate 754 has two electrodes shown in FIG. 7, electrodes 762 and 764. The electrodes shown in FIG. 7 may be implemented using any suitable conductive material, including transparent conductive materials such as but not limited to indium tin oxide (ITO). A hydrophobic coating (e.g. Teflon) may then be provided on the surfaces of the substrates 750 and 754 facing one another. A fluid droplet 775 is shown in FIG. 7 in the process of being aspirated into the capillary 750 or delivered from the capillary 750 into the region between the substrates 750 and 754. One substrate (e.g. the lower substrate) may also have a blanket insulating layer between the electrodes and the outer hydrophobic coating. In some cases (e.g. when CYTOP is used), the insulating and hydrophobic layer may be the same.

Substantially any fluids (e.g. liquids, aqueous liquids) may be used with the fixtures and microfluidic hubs described herein and introduced through fluid conduits in accordance with examples of the present invention. Examples include biological fluid samples, buffer fluids, reagents, aqueous and organic chemicals, acids, bases, ionic liquids, polymer gels, and the like. In some examples, fluids may contain particles, e.g. cells, viruses, proteins, analytes, labels, beads, biological molecules, chemical moieties, or other solid objects. In some examples, emulsions may be used such as a non-miscible carrier droplet may carry one or more smaller droplets (e.g. a surfactant-stabilized water droplet may be used which may have smaller, such as picoliter sized, double-walled phospholipid vesicles). In some examples, the fluid conduits may transport gases or supercritical fluids.

In some examples, fluid conduit tips may be positioned a distance away from an actuating electrode. For example, in FIG. 6, the capillaries 605 and 607 are shown positioned a distance from the electrodes 610 and 612. However, in some examples, the tip of one or both of the capillaries 605 and 607 may be positioned directly above or below the electrodes. A distance of approximately one-half electrode width away may be used in some examples, although other distances may also be used. As liquids are injected through the capillary and a droplet grows at its tip and approaches the critical actuation volume (e.g. the minimum droplet volume that can be actuated using the substrate electrodes), the voltage of the nearest electrode pad may be actuated. When the droplet reaches the critical actuation volume, the field generated using the neighboring electrode may cause the entire protruding droplet to jump off the end of the capillary and onto the electrode pad. The droplet (and any other droplets) may then be moved within the fixture using the electrodes without ever interacting with or contaminating the capillary inlet. This may reduce or eliminate opportunities for cross-contamination in sensitive assays. In an analogous manner, a droplet may be moved to a location proximate a fluid conduit (e.g. capillary) tip and may be aspirated into the fluid conduit located at or very near the boundary edge of the pattern electrode for removal from the fixture. Generally, and without being bound by theory, a droplet may have a spherical shape when not experiencing actuation energy, and may protrude past a boundary of one or more electrode pads. However, on actuation, the droplet may assume a shape closer to the electrode geometry. The changing shape of the droplet may be used to ensure contact with a capillary orifice in some examples. Droplet size may generally be related to the critical actuation volume (e.g. a volume slightly larger than the space above a single electrode pad, such that the droplet slightly overlaps neighboring electrode pads), and may be in the single microliter range, e.g. 2 microliters in some examples.

Figure 8A:
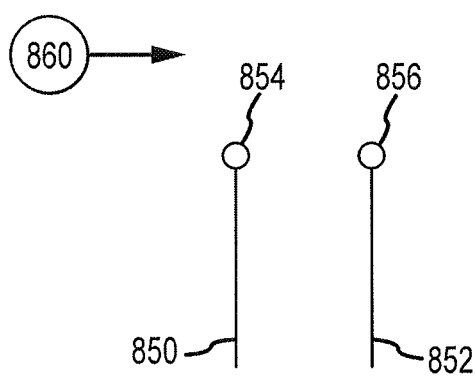
FIGS. 8A and 8B are schematic illustration of droplets being "plucked" off a capillary tip using a larger droplet in accordance with embodiments of the present invention.
Figure 8B:
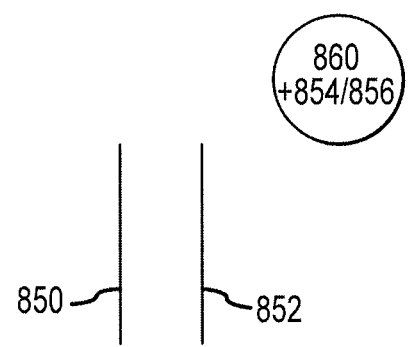

In other examples, droplets smaller than the critical actuation volume may be desired for mixing with other fluids. In conventional digital microfluidic devices, complicated dilution operations or quantized droplet merging and splitting sequences may be required to obtain a particular mixture of reagents. In examples of the present invention, smaller sized droplets may be incorporated into a larger droplet. FIGS. 8A and 8B are schematic illustration of droplets being "plucked" off a capillary tip using a larger droplet in accordance with embodiments of the present invention. Referring to FIG. 8A, the capillaries 850 and 852 are shown schematically. The capillaries 850 and 852 may be used, for example, to implement the capillaries 605 and 607 of FIG. 6 or any other capillaries described herein. The capillary 850 has a droplet 854 at its tip, and the capillary 852 has a droplet 856 at its tip. The droplets 854 and 856 may be less than the critical volume, e.g. they may be too small to actuate using the substrate electrodes. In some examples, the droplets 854 and 856 may have sub-microliter volumes, nanoliters in some examples. A larger droplet 860 of sufficient size to be moved using digital microfluidic technology may be moved past the droplet 854 and 856 (e.g. using electrodes patterned on a substrate defining a path of travel past the tips of capillaries 850 and 852). As the droplet 860 travels past the tips of the capillaries 850 and 852, the droplets 854 and 856 may merge into the droplet 860. Accordingly, once the droplet moves past, as shown in FIG. 8B, the droplet 860 may contain the fluid from the droplets 854 and 856. In this manner, smaller fluid volumes may be mixed into a droplet such that the droplet may contain a particular composition of mixed fluids. The fluids at the tips of the capillaries 850 and 852 in FIG. 8A may be delivered to the capillary tips from external fluid sources using, a direct (e.g. syringe pumps), indirect (e.g. thermal), or other fluid moving mechanisms.

The ability to introduce droplets to fixtures described herein with nanoliter precision in some examples may facilitate a variety of fluid operations that may take place within the gap between surfaces (e.g. substrates) in fixtures of embodiments of the present invention. Fluid operations that may be performed include, but are not limited to, serial dilution, droplet sub-sampling, chaotic mixing, fraction collection and sorting, magnetic bead manipulations, and sample archiving. Moreover, in some examples, droplets much larger than an individual electrode may be manipulated between substrates in examples of the present invention (e.g. by merging droplets together). Larger droplets may, for example, bridge continuously pumped inlet and outlet capillaries that may facilitate higher-volume fluid transfers using fixtures according to the present invention. For example, in some embodiments, capillaries described herein may be connected to a continuously-pumped fluid source and may continuously introduce fluid into the fixture.

Droplet delivery (and/or removal) may be automated. For example, one or more capillaries (e.g. the capillary 605, 607 or both of FIG. 6) may be connected to a fluid source which may be automatically controlled (e.g. through a syringe pump) to introduce fluid at a constant rate, or in periodic pulses. A power source may be coupled to an electrode positioned a distance away from the capillary (e.g. the electrode 610 or 612 or both of FIG. 6). The power source, e.g. an AC or DC voltage source, may be coupled to a printed circuit board that may be coupled to the electrodes through pads at a peripheral portion of the substrate, as has been described above. The power source may be controlled by a processor or other controller to activate a voltage to the electrode at a predetermined time selected to cause the droplet to release from the capillary and be positioned at the electrode. This automated process may be repeated as many times as desired.

Figure 9:
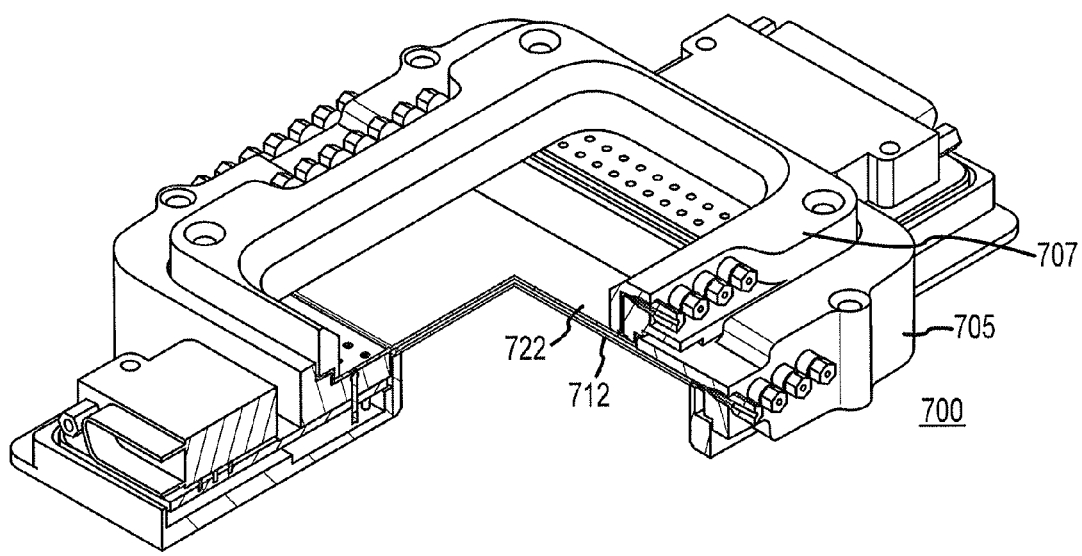
FIG. 9 is a quarter-section view of another fixture in accordance with an embodiment of the present invention.

Accordingly, embodiments of fluidic connection using fluid conduits (e.g. capillaries) positioned between substrates in a fixture have been described. In other examples, fluids may be introduced or removed from the fixtures through openings in one or more of the substrates. FIG. 9 is a quarter-section view of another fixture in accordance with an embodiment of the present invention. Similar to embodiments of the fixture 200 described above, the fixture 700 of FIG. 9 includes a frame 705 that may hold two substrates 712 and 722 at a predetermined substrate-to-substrate spacing. The frame 705 may be implemented using the frame 205 of FIGS. 2A and 2B. However, one or both of the substrates 712 and 722 may define holes that may be drilled, cut, or etched through the substrate. The compression member 207 used in FIG. 2 may instead in the embodiment of FIG. 9 be replaced with a compression member 707 that may define fluid paths between ferrules or other tubing connectors and the holes in the substrate 712.

Figure 10:
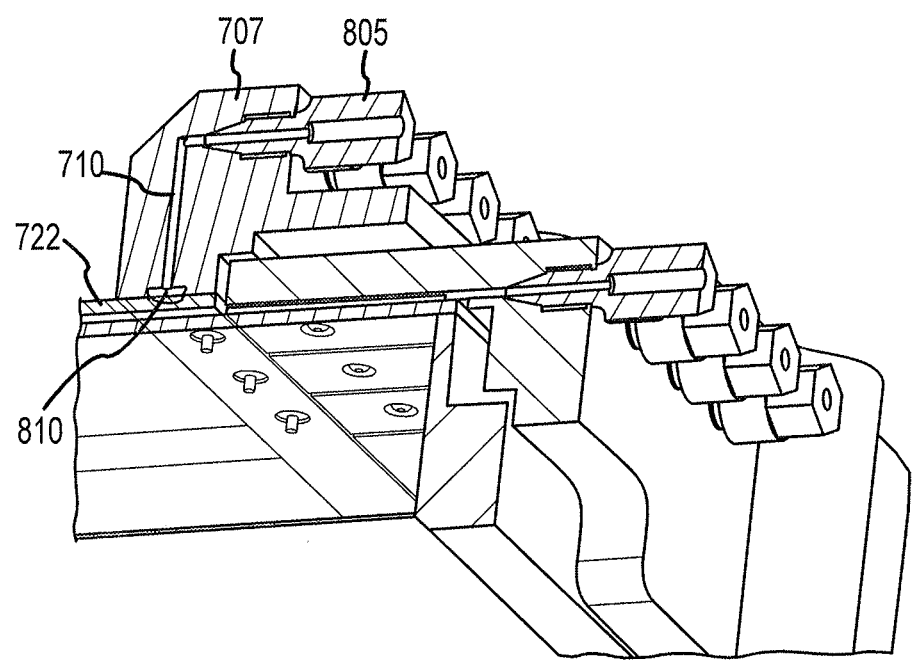
FIG. 10 is a close-up view of a cross-sectional portion of the fixture 700 of FIG. 9.

FIG. 10 is a close-up view of a cross-sectional portion of the fixture 700 of FIG. 9. The compression member 707 may define a fluid path 710 between a ferrule 805 and a hole of the substrate 722. Fluid may be introduced through the path 710 and a hole in the substrate 722 to the space between the substrates 722 and 712. The intersection between the compression member 707 and the substrate 722 may be sealed with a seal (e.g. an O-ring) provided on the compression member 707 or substrate 722. The compression member 707 may include recesses (e.g. recess 810) sized to contain an O-ring or other seal. A capillary may be inserted into the ferrule 805, and fluid provided through the capillary into the fluid path 710. In some examples where ferrules may not be used, machined channels may be replaced by capillary or tubing potted into the compression member 707, providing an option for smaller internal fluid volumes. For either design, once a substrate is positioned in the pocket of the frame, the compression member 707 may be positioned on it and tightened into place, compressing any compliant electrical contacts as described above, and pressing the face of the substrate against the registration surface as also described above, but also in examples employing the fluid connection of FIG. 10, compressing O-rings or other seals around the drilled substrate holes to form a gas- or watertight seal to the outer surface of the substrate 722. Embodiments using fluid delivery through substrate holes may enable robust fluidic delivery and withdrawal to and from the system while allowing the use of gap spacing between substrates that may be smaller than the smallest commercially available or practical capillary tube. Embodiments of fluid connections using holes in the substrates may be used instead of or in combination with fluid connections using capillaries inserted into the gap between the substrates, as is shown in FIGS. 9 and 10, where the fluid connections to holes in the substrate are shown in addition to the fluidic connections along the side of the frame.

Embodiments of fixtures described herein may further include sealed device areas and/or pressurized sections of the region between substrates. In contrast to designs where a spacer element sets the substrate-to-substrate distance and also serves as the seal, embodiments of the present invention may set substrate-to-substrate spacing using examples of fixtures described herein, which may be independent of the selection, geometry, and fabrication of a sealing gasket itself. Moreover, the compression force provided by the two-sided compression members discussed herein may advantageously provide options for sealing even under pressure.

In some embodiments, a compliant cut gasket may be inserted between the two substrates in a fixture (e.g. substrates 212 and 222 of FIGS. 2A and 2B) or a large diameter, small cross-section O-ring may be inserted between the substrates. Because substrates are pre-positioned relative to each other by the frame 205, in some embodiments, lithographically defined gaskets may be fabricated while the substrates are in the fixture 200. For example, a photoresist or photosensitive polymer may be introduced between the substrates 212 and 222 of FIG. 2A (e.g. using the fluid ports described herein). The photoresist or photosensitive polymer may then be exposed in desired portions to solidify, cross-link, polymerize, or otherwise set the material in situ. Examples of in situ seals formed in this manner may seal around pre-positioned in-plane capillaries described herein. For seals formed by photopolymerization or cross-linking, the internal space between the substrates 212 and 222 may be partially flooded with liquid precursor, selective exposure applied to solidify the seal, then remaining liquid precursor flushed out of the device through in-plane or through-hole fluidic interconnects described herein. Alternately, in some examples, gaskets could be cast in situ around in-plane capillaries by depositing a continuous bead of gasket material (e.g. room-temperature vulcanizing silicone, polydimethylsiloxane, etc.) on one or both substrates before positioning them in the substrate frame with in-plane capillaries already in place. The gasket material may then conformally seal around the capillaries as it cures in place provided a material is selected which does not shrink prohibitively during solidification.

Simple hermetic sealing of the space between substrates in example fixtures of the present invention (e.g. by installing a gasket only) may prevent or reduce transfer of contaminants from the environment into the assembled device or vice versa. Hermetic sealing also may serve to mitigate droplet volume loss due to evaporation. Hermetic sealing of the example of FIGS. 2A and 2B, however, may be more challenging as in-plane capillary interconnects may be difficult to use in conjunction with a gasket. In contrast, examples of through-hole fluidic as shown in the example of FIG. 10 may advantageously facilitate a variety of potential sealed and quasi-sealed modes of operation when the gasket seal is made outside the position of the substrate through holes. With the exception of through-hole connections, the compressed gasket may completely isolate the space between the substrates from the surrounding environment, a functionality that may be facilitated by the compression force resulting from the compression members and frame used to assemble examples of fixtures described herein.

Using the fluidic access provided by the through-substrate holes, such as those shown in FIG. 10, the space between substrates may be maintained at particular environmental conditions, such as a humidity or pressure, or combinations thereof, in some examples. The area between the substrates may also be purged with dry/inert gas for conducting oxygen- or moisture-sensitive reactions or different gas mixtures can be introduced for cell culture and viability experiments, and/or atmospheric-sensitive reactions. Examples of such sealed devices may function as a first-line safety barrier when working with Biosafety Level 4 highly-infectious agents. Pressurization or partial evacuation of the area between the substrates may be used to moderate or speed up evaporative processes or to degas droplets in situ. In particular, for devices including integrated heaters, sealing or pressurization may enable higher temperature droplet manipulations without boiling or significant volume loss due to evaporation (e.g. for on-fixture polymerase chain reactions or PCR). Similarly, using examples of through-substrate fluidic connections, the area between the substrates chamber may partially or completely flooded with liquid or vapor to allow multiphase liquid-liquid experiments and droplet manipulations (e.g. water in oil, etc.) or to decontaminate the system by bulk flushing of the interstitial space with bleach or vaporized hydrogen peroxide.

For pressurized operation, reinforced compression members may be used in which each compression member may include a pair of webs or stringers positioned to provide compression forces normal to the substrate and just inboard of the registration surfaces of the frame. In the normal direction, these reinforcing webs may overlap the long edges of the opposing backing frame and may be designed to provide two-sided compression for a square cut gasket occupying a periphery of the frame window. Examples of reinforced frame designs may advantageously form a robust seal even under moderate pressurization (e.g. several psi). Depending on the degree of pressurization required, additional backing frame reinforcement may be used, including reinforcing webs which further subdivide and support the window defined by the frame. Partially evacuated operation may be more challenging and may be facilitated by use of rigid stand-offs or spacers between the substrates to prevent them from flexing inward or bonding the reinforcing elements of the backing frame to the outer surfaces of the substrates to maintain the desired substrate-to-substrate gap spacing.

The ability to hermetically seal and pressurize or evacuate one or more areas between substrates of example fixtures described herein may facilitate additional modes of operation. Rather than always moving liquid on or off the fixture using a syringe or other positive displacement pump, for example, pressurization of one or more areas between the substrates may be used to drive liquid from the area between the substrates into through-hole fluidic ports or capillaries for interface to other fluidic modules, even those requiring pressure driven flow (e.g. chromatography columns, etc.). Similarly, negative pressure between the substrates may draw liquids onto the fixture from connected capillaries and other subsystems. In either case, liquids may be selectively delivered or aspirated by actuating a valve connected to the appropriate port, rather than requiring a dedicated pump.

Embodiments of systems and fixtures described herein accordingly include microfluidic hubs having fluidic conduits that may be used to introduce and/or remove fluids from a space between surfaces, where the space between the surfaces may be defined by a frame. As has also been described, droplet actuators (e.g. digital microfluidic technology) may be used to move fluid droplets in a controlled manner. Accordingly, the microfluidic hubs described herein may be used to move fluid droplets from one input fluid conduit to another output fluid conduit, or in and out of the microfluidic hub through a same conduit.

Figure 11:
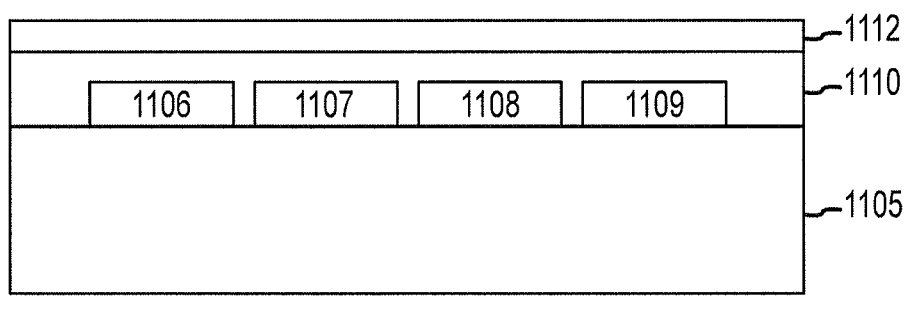
FIG. 11 is a schematic illustration of a cross-section of a substrate in accordance with embodiments of the present invention.

Implementation of electrodes or other components on substrates described herein that may be used in microfluidic hubs described herein is quite flexible. For example, electrode designs may be implemented on one or both of the substrates 212 and 222 that may be selected to facilitate particular digital microfluidic applications. FIG. 11 is a schematic illustration of a cross-section of a substrate in accordance with embodiments of the present invention. The substrate 1100 may, for example, be used to implement the substrate 212 or 222 of FIGS. 2A and 2B, or other substrates described herein. As generally described above, the substrates may include a bulk substrate material 1105. The bulk substrate material 1105 may be implemented using any of a variety of materials, including but not limited to glass, quartz, silicon, polymers, metals, or combinations thereof. In some examples, the bulk substrate material 1105 may be a glass slide. The bulk substrate material 1105 may support electrodes 1106-1109. Any number and shape of electrodes may be used. The electrodes may be formed of a conductive material which may be implemented using, for example, conductive ITO, chrome, or gold. In one example, a thin film (e.g. <200 nm layer) of ITO may be used to define the electrodes, pads, and traces that may be present on a substrate. Other conductive materials may also be used. The electrodes may be present on the substrates in a desired electrode pattern. Such a pattern may be achieved using any suitable technique for creating a pattern of material. Photolithography, wet or dry etching, or deposition techniques including sputtering or chemical deposition, or combinations of these techniques may for example be used. In some examples, photolithographic patterning of a conductive material film followed by wet chemical etching may be used to provide the patterned electrodes and pads. In some examples, electrode patterns may be created by directly writing the conductive film (e.g. chrome, ITO) with a laser to selectively remove the conductive material from the bulk substrate. In some examples, the electrodes 1106-1109 may be 2.5 mm square, which may correspond with a droplet volume of approximately 1.2 microliters in a fixture having a gap spacing between substrates of 185 microns. Spacing between the 2.5 mm square electrodes may be 20 microns, although other spacing may be used.

The substrate 1105 may further include an insulating material 1110 for insulation between the substrate and the region between substrates, e.g. in some examples a 4 µm conformal layer of vacuum-deposited parylene-C may be used to implement the insulating material 1110. The parylene may be any suitable thickness, 1-2 microns in one example. Other insulating materials and deposition techniques may also be used. In some examples, the insulating material itself may be hydrophobic and no further surface treatment may be provided. In other examples, a hydrophobic surface treatment 1112 may be provided, e.g. a Teflon AF coating. Contact pads may be exposed by any suitable material removal technique (e.g. wet or dry etching) so the pads are available for electrical connection to interconnects of fixtures described herein.

Figure 12A:
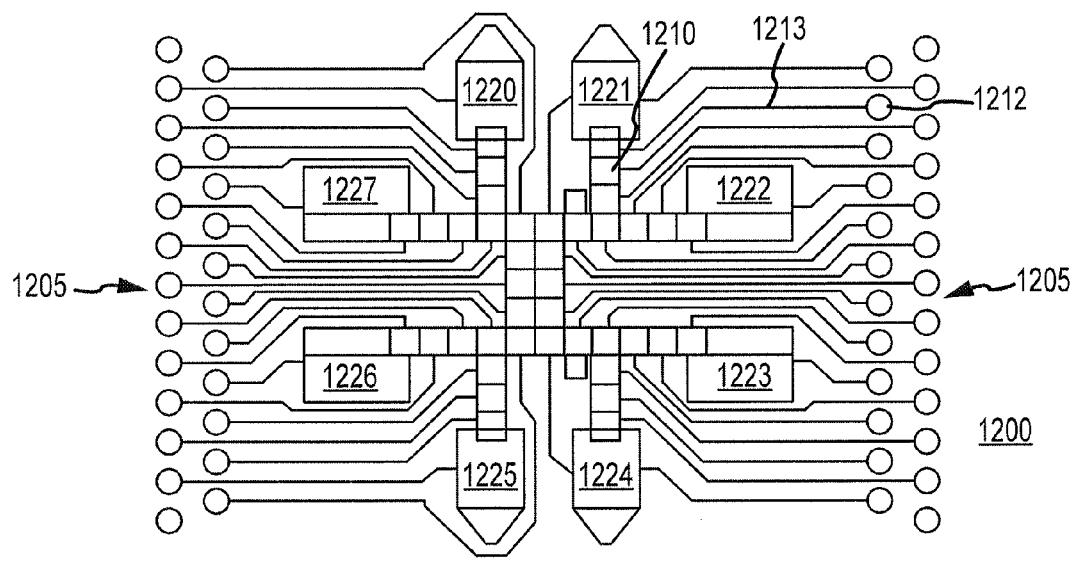
FIGS. 12A and 12B are schematic illustrations of electrode patterns that may be used in embodiments of the present invention.
Figure 12B:
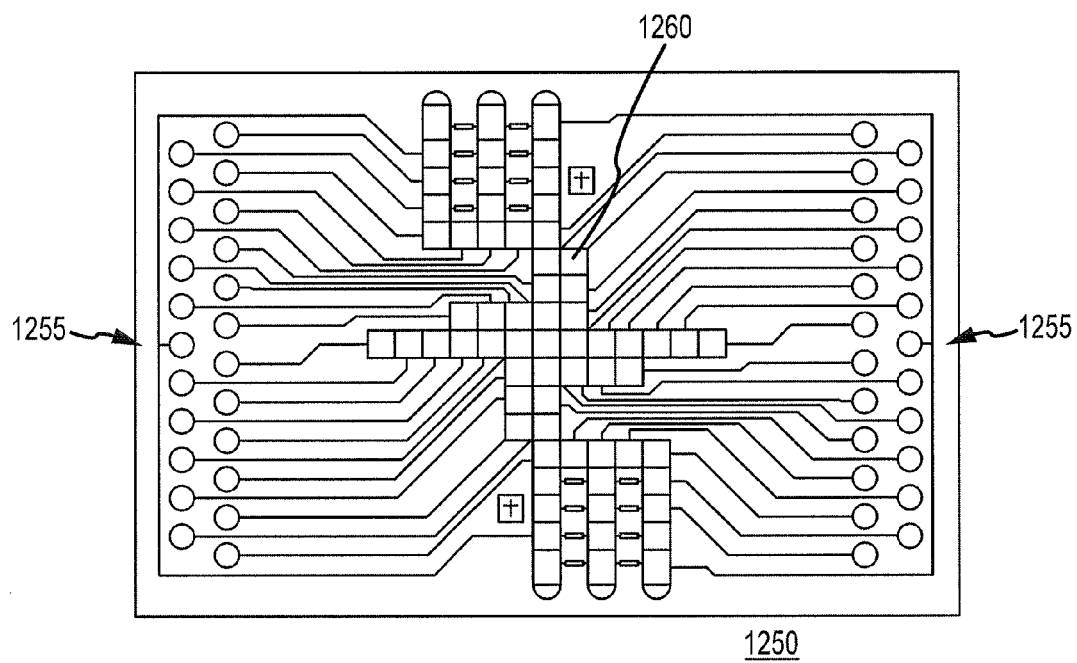

As described above, electrodes may be provided on substrates in any pattern desired for performing particular applications. FIGS. 12A and 12B are schematic illustrations of electrode patterns that may be used in embodiments of the present invention. The electrode pattern 1200 of FIG. 12A may, for example, be used on the substrate 222 of FIGS. 2A and 2B. The electrode pattern 1200 may include a number of pads 1205, 46 are shown in FIG. 12, for connecting to the electrical contacts on a frame into which the substrate containing the electrode pattern 1200 may be positioned. For example, referring back to FIGS. 2A and 2B, the pads 1205 defined by the electrode pattern 1200 may interface with the holes in the fixture 205 that may have pogo pins or other conductive connectors.

Referring again to FIG. 12A, electrodes may be provided that may generally be of a uniform size for moving fluid droplets. One such electrode is labeled 1210 in FIG. 12. These uniformly-sized electrodes may be considered "stepping stones" for moving droplets. Each uniformly-sized electrode may be connected to a corresponding pad by a conductive trace, e.g. the electrode 1210 is connected to pad 1212 by trace 1213. In a similar manner, other pads are connected to electrodes shown in FIG. 12. The uniformly-sized electrodes, including the electrode 1210 accordingly provide "paths" on a substrate along which a droplet may be controlled to move. Larger electrodes may also be provided that may serve as reservoirs for a larger fluid volume. Larger electrodes 1220-1227 are shown in FIG. 12, and each larger electrode may also be connected to a respective pad for electrical addressing. It is to be understood that in some examples more than one larger electrode and/or uniformly-sized electrode may be addressed using a same pad. In some examples, capillaries may be positioned to introduce or remove fluids proximate to the larger electrodes 1220-1227 and/or uniformly sized electrodes, as has been described above. Accordingly, the larger electrodes 1220-1227 may be positioned and spaced apart in accordance with the location and spacing of ports in a particular frame. In some examples, the reservoir electrodes 1220-1227 may be the same size as the uniformly-sized electrodes, and in some examples the uniformly-sized electrodes may not all have a uniform size. The edges of the electrodes 1220, 1221, 1225, and 1224 have a tapered shape. The tapered shape may facilitate interfacing with through-holes in a substrate above or below the surface on which the electrode pattern 1200 is fabricated, which may be present with or without in-place fluid conduits inserted through a frame as described above. Accordingly, the tapered edges may be provided on locations of a substrate corresponding with the locations of through-hole on the same or an opposite substrate. The uniformly-sized electrodes and larger electrodes are arranged to provide fluid paths between the reservoirs defined by the larger electrodes. By actuating an appropriate sequence of uniformly-sized electrodes, for example, fluid droplets may be moved from the reservoir 1227 to 1222, or from reservoir 1227 to any of the other reservoir electrodes, by sequentially activating (e.g. providing voltage to) the series of uniformly-sized electrodes along the path between the two desired reservoir electrodes.

The electrode pattern 1250 of FIG. 12B may also, for example, be used on the substrate 222 of FIGS. 2A and 2B in other examples. The electrode pattern 1250 may also include a number of pads 1255 for connecting to the electrical contacts on a frame. The electrode pattern 1250 may also include a plurality of uniformly-sized electrodes, including the electrode 1260, where the uniformly-sized electrodes may each be connected to one of the pads 1255 or groups may be connected to individual pads. No larger electrodes are provided to serve as reservoirs in the example of FIG. 12B. The rounded edges of the electrodes at the top and bottom of the pattern 1250 may facilitate interaction with through-holes above or below the rounded electrodes.

Figure 13:
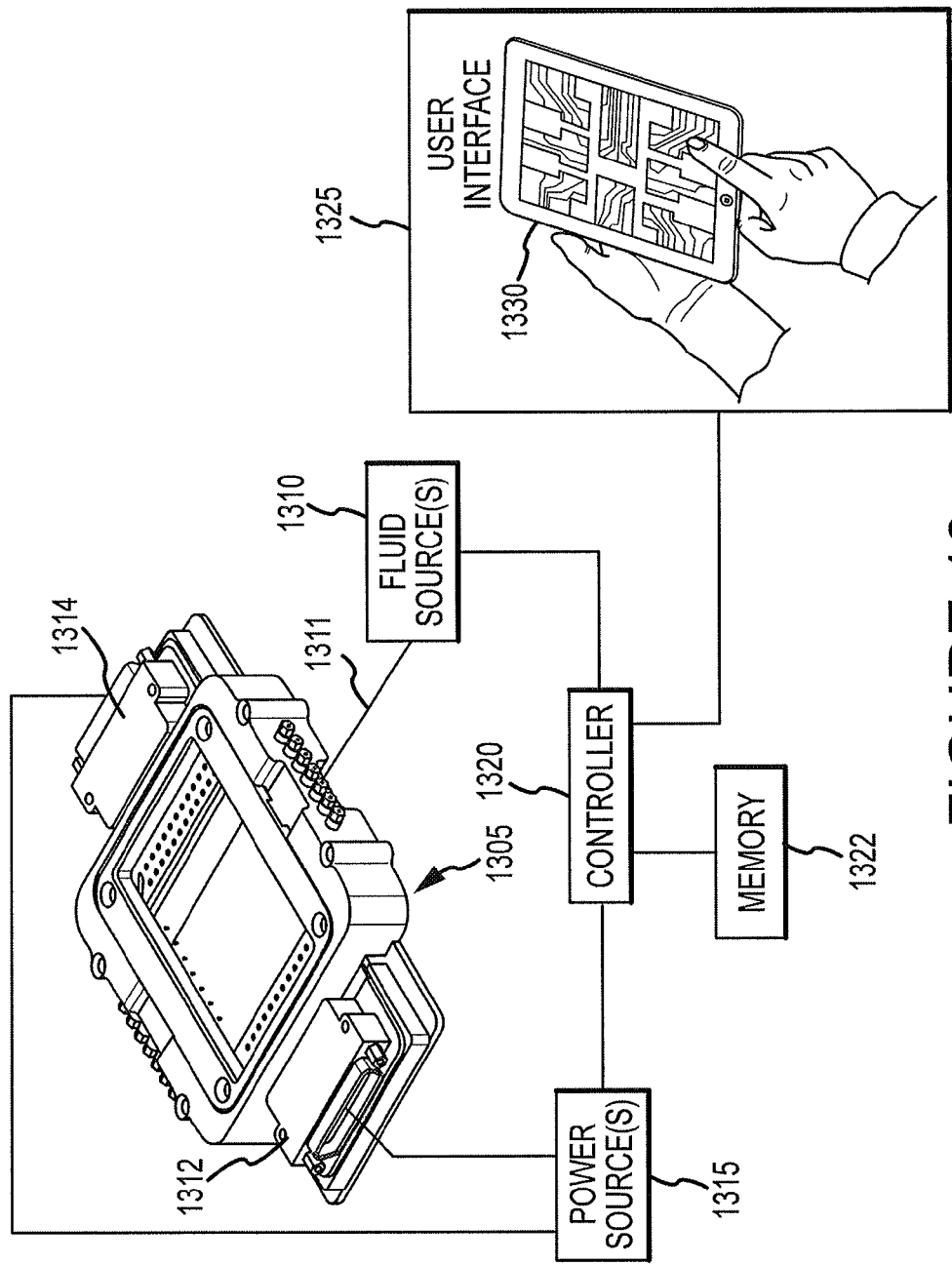
FIG. 13 is a schematic illustration of a system arranged in accordance with embodiments of the present invention.

Fixtures and microfluidic hubs in accordance with embodiments of the present invention may form part of systems used to perform applications involving a series of manipulations with fluids within the fixtures. FIG. 13 is a schematic illustration of a system arranged in accordance with embodiments of the present invention. A microfluidic hub 1305 may include substrates and fluidic and electrical interconnections, as has been described above. For example, the fixture 200 of FIGS. 2A and 2B may be used to implement the microfluidic hub 1305. As described above, the microfluidic hub 1305 may include access ports for fluid conduits. The microfluidic hub 1305 may include the fluid conduits, e.g. fluid conduit 1311. The fluid conduits may be connected to one or more fluid sources 1310. The fluid source(s) 1310 may include one or more reservoirs or outputs or inputs of other fluidic systems. The fluid source(s) 1310 may include mechanisms for driving fluid flow, e.g. pumps and/or valves, which may be controlled as described herein. The microfluidic hub 1305 may also include electrical connections to substrates within the fixture 1305. The electrical connections may be accessible through connectors 1312 and 1314, which may be standard electrical connectors. As described above, the microfluidic hub 1305 may include one or more printed circuit boards to provide some electrical routing and/or components within the fixture 1305.

The electrical connections may be coupled to one or more power source(s) 1315. The power source(s) may include one or more voltage sources, including AC and/or DC voltage sources, current sources, or combinations of voltage and current sources. The power source(s) may include circuitry to condition or otherwise route the power provided by the power source(s) including, for example, function generators, AC high-voltage amplifiers, solid-state relays, or combinations thereof. In some examples, relays are provided that may receive control signals to provide one of three possible power states (e.g. high, ground, or float) to each of the pads exposed by the fixture 1305. In one example, AC voltages of 50 Vrms to 150 Vrms at 15 kHz may be used to actuate electrodes on a substrate in the fixture 1305. Generally, AC voltages in the range of 50-120 Vrms at frequencies in the vicinity of 15 kHz may be used for closed-format droplet actuation in digital microfluidic systems. The applied voltage used may vary depending on variables including the conductivity of the droplet and the spacing between top and bottom substrates. Alternative modes of droplet manipulation may include the application of DC voltages. An array of Aromat-style solid state relays may provide AC/DC actuation and ground voltages to the electrode pads on example fixtures described herein. AC actuation voltages may be produced by driving a high voltage piezoelectric amplifier with a function generator to achieve the desired frequency and voltage for droplet actuation. Three state (high, float, ground) functionality may be provided by cascading relays. This same approach may be used to provide AC-high, DC-high, and ground signals to the electrode pads as needed.

A controller 1320 may be provided that may provide control signals to the power source(s) 1315 and/or fluid source(s) 1310. The control signals may control timing of the applied power and/or fluids to the fixture 1305. The controller 1320 accordingly may control fluid pumps, valves, relays, circuits, or other electronics associated with either the fluid source(s) 1310, power source(s) 1315, or both. The controller may be implemented using any controlling circuitry or software suitable for controlling the fluid and/or power sources of the system 1300. Examples include, but are not limited to, computers including one or more processors and/or ASIC circuits. Memory 1322 may be coupled to the controller 1320 and may store executable instructions for causing the controller 1320 to control the fluid source(s) 1310 and/or power source(s) 1315 in a particular manner. For example, the memory 1322 may store instructions for causing the controller 1320 to provide control signals to move one or more droplets through the fixture 1305 and/or perform any of the droplet operations described above. In this manner, fluid operations involving the fixture 1305 may be automated. A user interface 1325 may be provided and may be coupled to the controller 1320 for user operation of the system 1300. Any of a variety of input and/or output devices may be used to implement the user interface 1325, including one or more displays, keyboards, mice, touchscreens, or combinations thereof. The user interface 1325 may be integrated with the controller 1320 in some examples (e.g. a computer may include a processor that serves as the controller 1320 and be coupled to input and/or output devices for causing the processor to perform selected functions). In some examples, a remote computing device may be supplied that may be in communication with the controller 1320 over a wireless or wired network.

A separate computer may be used to provide the user interface 1325, for example. In one example, a tablet computer 1330, cellular telephone, or other user computing device with processing capability (e.g. iPad, iPhone, Android devices, etc.) may be used to provide the user interface 1325. The tablet computer 1330 may have sufficient processing and memory capability to display status information regarding the fixture 1305 and/or allow a user to control the system 1300. In one example, the tablet computer 1330 may display the electrode layout present on one of the substrates of the fixture 1305, for example. A user may control the system 1300 by touching locations of the display corresponding to electrodes that the user desires to activate, for example. In other examples, the user may select particular programs, which may be stored in the memory 1322 and/or in the memory of the tablet computer 1330 to select a particular automated operation of an experiment or assay in the fixture 1305. In some examples, a display may display electrode locations and keyboard assignments (or other user input actions) associated with each electrode location or desired program.

Accordingly, power (e.g. voltage) switching and electrode state (e.g. high, ground, floating) may be communicated from the user interface 1325 to the controller 1320. In some examples, closed-loop control (e.g. machine vision or electronic sensing) may be used to verify droplet actuations, and the appropriate sensors may be coupled to the controller 1320 for closed-loop control. In some examples, fluorescence or impedance measurements may be made to track the arrival of samples of interest through fluid conduits (e.g. in-plane capillaries) so they can be captured dropwise for, e.g. fraction collection. Suitable sensors may similarly be coupled to the controller 1320. In some examples, the controller 1320 may accordingly be configured to measure conductivity or capacitance at a particular location or locations within the microfluidic hub to verify or determine a droplet location. Electrodes may be manually activated by a user, or a user may initiate an automated sequence of activations. In some examples the controller and/or user computing device (e.g. tablet computer 1325) may provide a scripting interface that may be used to create an automated sequence of electrode activations. The interface may provide a vocabulary of pad actuation primitive operations (AC pulse, move ground, etc.) or more complex sequences of droplet maneuvers. In this manner, a user may select the droplet operation desired and schedule the droplet operation effectively. A user may select a sequence of droplet operations and/or movements and store the sequence as a script in, e.g. the memory 1322 or other memory accessible to the controller 1320. For real-time control, users may simply press the appropriate key or touch the appropriate area, or perform other assigned action, on the user interface to actuate the desired pad, including in some examples the ability to perform multiple simultaneous actuations to enable operations like droplet splitting and stringer formation. Software may also allow users to manually trigger actuation voltage pulses of specified duration, which may be advantageous in establishing preferred droplet actuation parameters for automated scripting. The controller 1320, or another controller in the system, may provide device drivers for controlling and sequencing other components in the system—e.g. pumps, valves, heaters, or other components.

Although not shown in FIG. 13, optics may also be provided with the system 1300. One or more microscopes, cameras, or optical objectives may be provided for viewing areas of the substrates exposed by the fixture 1305. The optics and/or detectors may be moveable, and the motion may also be controlled, for example, by the controller 1320. The user interface 1325 may display a picture and/or detection data received from optical detectors provided in the system 1300.

Examples of microfluidic hubs and systems using microfluidic hubs, which may include fixtures as described herein. Fluids may be introduced to microfluidic hubs described herein from fluid reservoirs or other fluid modules. The fluids may be moved, reacted, mixed, or otherwise manipulated within the microfluidic hub, for example using digital microfluidic techniques. The fluids may be transported out of the microfluidic hub and into other reservoirs or other fluid modules. Generally, while within the microfluidic hub, the fluids may be manipulated in discrete fluid droplets, however the microfluidic hub may interface with continuous flow fluidic systems. There are a variety of techniques for handling fluids that may not be readily integrated using conventional techniques (e.g. digital microfluidics, pressure-driven continuous flow fluidics, droplet microfluidics, electromigration-based systems, capillary-based systems, etc.). Sometimes, a particular fluidic technology may be best suited to perform a particular fluid processing technique. However to create a truly integrated fluidic handling and analysis system, it may be advantageous to connect these disparate systems together. Embodiments of microfluidic hubs according to the present invention may provide such integration by providing simple fluidic connection and manipulation capability between any systems that may be capable of inputting or outputting to a fluid conduit that may be used with embodiments of microfluidic hubs described herein.

In some examples, microfluidic hubs described herein may allow parallel operations with multiple combinations and permutations of different events. For example, fluid droplets may be introduced through one fluid conduit and manipulated in a particular manner while another fluid droplet is introduced through another fluid conduit at a different location in the hub, and may be manipulated in a different manner. Fluid manipulations can accordingly occur in parallel.

Moreover, in some examples, fluid conduits (e.g. capillaries) may themselves be utilized as tubes, microreactors, or containers to carry out multiple incompatible operations in an automated fashion. That is, fluid droplets may be aspirated into a fluid conduit, for example, and an operation performed on the fluid accumulated within the fluid conduit. Any fluidic operation able to be conducted in the fluid conduit may be performed. The fluid may then be returned to the microfluidic hub, for example by pressure-driven or other flow and actuation of appropriate electrodes to provide the fluid, droplet-by-droplet, into the microfluidic hub.

Figure 14:
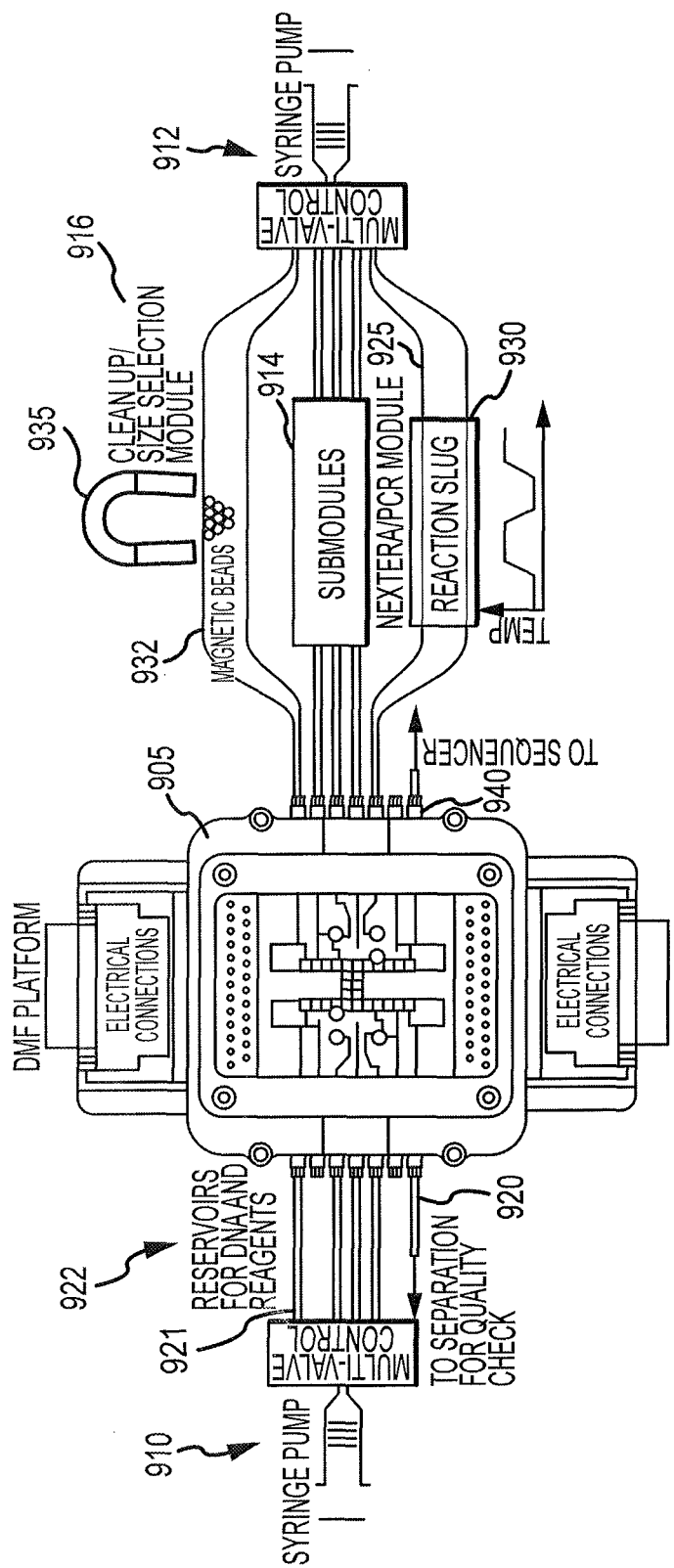
FIG. 14 is a schematic illustration of a fixture integrated into a larger microfluidic system in accordance with embodiments of the present invention.

FIG. 14 is a schematic illustration of a microfluidic hub including a fixture integrated into a larger microfluidic system in accordance with embodiments of the present invention. The example of FIG. 14 is a system configured to perform the Nextera protocol for next generation sequencing DNA library preparation. This functionality is exemplary only, and systems may be assembled using the modular techniques described herein to perform other functions in other examples. A microfluidic hub 905, which may be implemented for example using the fixture 200 of FIGS. 2A and 2B or the fixture 700 of FIG. 8, may be coupled to other submodules 914 using the capillary fluid interface. Two syringe pumps and multiport valves 910, 912 are used to deliver sample and reagents to the fixture 905 and other capillary-connected submodules. While syringe pumps and valves are shown, substantially any fluid driving mechanism may be used in other examples. The submodules may include, for example, a thermal cycler for performing library enrichment by polymerase chain reaction (PCR), a magnetic bead-based DNA size-selection and clean-up module 916, and a high-temperature enzymatic microreactor module for performing DNA fragmentation. A capillary electrophoretic separation may be performed directly in one of the fluid conduits, e.g. capillary 921, to provide quality control monitoring of the library preparation process. In this notional example, the microfluidic hub 905 may mediate the delivery of fluid droplets among various analytical subsystems and fluid modules.

DNA library construction or preparation may be a required step to format DNA for sequencing on instruments that implement the sequence using a synthesis method. Library preparation procedures may be one of the major bottlenecks for next generation sequencing. However, new protocols like the Nextera protocol may help to streamline the workflow by using a transposon-based method for preparing fragmented and tagged DNA libraries for sequencing.

The example of FIG. 14 is a system configured to execute the four consecutive steps of the Nextera protocol for next generation sequencing DNA library preparation. Each function for executing the protocol is implemented as modules interfaced to the microfluidic hub through fluid conduits. The exact position or relative position of modules in the example of FIG. 14 may be altered or rearranged in other examples with no or minimal effect on the output. The desired amount of sample DNA to be prepared for sequencing may be delivered to the microfluidic hub through a fluid conduit (e.g. capillary 921) using a positive displacement syringe pump 910. The droplet may increases in size on the end of the fluid conduit until the desired amount is delivered and actuated away within the microfluidic hub 905, as has been described above. Likewise other fluid conduits (e.g. capillaries 922) containing reagents for the Nextera reaction (e.g. enzymes, buffers, wash fluids, magnetic beads, decontamination fluids) may be stored in fluid conduit (e.g. capillary) reservoirs that are connected to the microfluidic hub and delivered appropriately by switching an external valve (e.g. multi-control valve shown coupled to the syringe pump 910) and dispensing the desired amount of reagent. In this manner, fluid conduits may serve as reservoirs, storing fluids for later dispensing into the space between surfaces in the microfluidic hub of FIG. 14, and/or receiving fluids from the space between surfaces in the microfluidic hub of FIG. 14.

To start the Nextera reaction, the DNA droplet delivered to the microfluidic hub 905 may be actuated away from a capillary tip, merged with an appropriately sized transposase enzyme in buffer droplet and then mixed in the fixture. Mixing may be accomplished by applying voltage to neighboring electrodes in sequence to move the merged droplets to homogenize the mixture. Once mixed, the droplet may be actuated to a capillary interface for a capillary coupled to the Nextera reaction module 925 and the entire droplet contents may be aspirated off of the fixture and into the microreactor 930 embedded in a thermal heater block. A reaction may be carried out in the module 930 and the resulting product (e.g. fragmented and tagged DNA) may be reintroduced to the fixture of the microfluidic hub by activating a syringe pump 912, for example.

Next, the fragmented DNA may require a clean-up or buffer exchange in preparation for subsequent DNA amplification. The clean-up may be accomplished by mixing DNA-binding magnetic particles with the fragmented DNA on the microfluidic hub (e.g. within the fixture). The magnetic particles may be introduced to the microfluidic hub (e.g. introduced into the fixture) in a fluid droplet. The magnetic particles may for example, be stored in one of the capillaries 922. After mixing together within the fixture, beads now with bounded DNA may be actuated into position to be aspirated into a clean-up module (e.g. a capillary or reservoir), such as the clean-up capillary 932 shown in FIG. 14. In the module 932, externally positioned permanent magnet traps 935 may be positioned to hold the beads in a specific location inside the capillary while the supernatant fluid containing the used enzyme, old reagents, and buffers are removed. Subsequent washings and a final rinse with elution buffer, may disassociates the DNA from the beads into clean buffer.

The purified DNA may then be reintroduced to the microfluidic hub 905 (e.g. the fixture) for the next step: amplification. DNA may now be mixed with amplification reagents within the fixture, and may be introduced into the PCR module 925 to carry out, for example, 6-10 cycles of a temperature cycle to amplify the DNA sample. While the PCR module is shown as the same module as the Nextera reaction module in FIG. 14, in other examples different reaction modules may be used for these functions. The PCR products may be delivered to the microfluidic hub and size fractionated using magnetic beads and washing steps that may occur using droplet manipulations within a fixture described herein. After size-selection, the product may be ready for loading onto the sequencing instrument through port 940 shown in FIG. 14. A library validation may be carried out with a QC module 920 to determine the DNA amount and overall size distribution. The sample DNA may be prepared for analysis by adding small amounts of fluorescent DNA dye and internal ladder standards. The QC module 920 may use a separation capillary filled with polymer gel for sieving the DNA. The droplet may be actuated into position within the microfluidic hub 905 and interfaced with the separation capillary 920. Rather than pumping the sample, the charged DNA molecules may be electrophoretically driven into the inlet of the capillary by applying an electrical field. The electrical circuit is completed with a thin electrically conductive wire opposite to the capillary but also in contact with the droplet. A small applied voltage gradient may electrophorese the DNA into the separation capillary, after which the droplet may be actuated away, breaking the electrical circuit. A run buffer droplet may now be positioned at the interface and the electrical circuit reestablished. The run voltage is applied and size distribution of the products may be measured with a readout of the fluorescence. The internal standards provide a method for calibration and validating the Nextera preparation steps and providing the guidelines for titrating the finalized DNA product for sequencing.

Embodiments of system and fixtures described herein may be used in a variety of fluidic applications. As described above, the fixtures may be used to perform droplet operations used in digital microfluidic technology. An example system for performing the Nextera protocol for next generation sequencing DNA library preparation was also described above. There are many other uses and applications to which systems and fixtures in accordance with the present invention may be put.

Embodiments of the present invention may include serialization and/or deserialization of fluid droplets. Examples of in-plane capillary interfaces described above (and potentially the through-hole interfaces in some examples) may facilitate the generation of "trains" of heterogeneous fluid components for delivery to off-fixture assays or processing modules. In one example, serialization may occur as follows. Referring back to FIG. 12A, for example, in a microfluidic hub including a substrate having the electrode pattern 1200, a fluid conduit (e.g. capillary) may be provided proximate the electrode 1223 using the interconnection techniques described above. A syringe pump may be coupled to the fluid conduit. The syringe pump may apply a negative pressure to the fluid conduit. Fluid droplets may be moved along the "stepping stone" electrodes by sequentially activating the electrodes to move a droplet toward the electrode 1223. When a droplet reaches the electrode 1223, it may be aspirated into the fluid conduit. A next fluid droplet (which may be a droplet of a different fluid) may be moved into position, and the next droplet aspirated into the capillary. This process may continue, moving subsequent droplets of fluid into position, and pulling in those droplets. In this manner, a segmented stream of different fluids with unique composition may be contained in the fluid conduit and delivered to another location through the fluid conduit in an orderly fashion. Similarly, air bubbles may be pulled in during this process to create a series of discrete fluid boluses in the capillary. The discrete fluid boluses may prevent or reduce mixing and/or provide readily detectable markers for closed loop process control. For example, one or more droplets of a first fluid may be pulled into the fluid conduit, followed by an air bubble, followed by one or more droplets of a second fluid. In this manner, a discrete bolus of first and second fluids may be captured in the fluid conduit. Similarly, when a segmented fluid train is delivered to the substrate, droplets corresponding to different fluids or different samples can readily be retrieved from the fluid conduit in piecewise fashion, by sequentially transporting droplets away from the fluid conduit. In this manner, "deserialization" or reorganization of the segmented flow back into separate homogeneous phases may occur.

Examples of microfluidic hubs and systems in accordance with the present invention may operate as a fraction collector. In many applications, it may be desirable to subsample a larger volume of liquid to concentrate the constituents of interest or otherwise isolate them from the larger bulk of solvent. One example is an electrophoretic or chromatographic separation in which different species migrate through a channel at different rates and are spatially separated in serial fashion in the separation column as a result. Once separated, separated sample constituents typically move past a detector (fluorescence, conductivity, etc.) generating a signal indicating the relative abundance of each constituent and its time of arrival at the detector as a train of spatially and/or temporally separated peaks in the output of the detector. While this train of "peaks," concentrations and rarefactions of constituents of interest, exists as a continuous slug or background of liquid, subsampling and discretization can be accomplished by delivering this sample slug to an example microfluidic hub in accordance with the present invention. As the sample emerges serially from an in-plane capillary, for instance, a droplet grows at the end of the capillary, eventually reaching a critical actuation volume, at which point the droplet may be moved away from the capillary outlet. By coordinating this droplet actuation activity with the output of a detector upstream, the microfluidic hub may allow droplets corresponding to regions of interest (e.g. high concentration, specific peaks, etc.) in the separation to be pulled aside for short-term storage or subsequent operations, while droplets associated with uninteresting regions may similarly be collected and discarded, all in piecewise fashion. For example, a detector may identify a portion of the stream of interest, and the electrodes on a substrate may be actuated to draw that portion of the stream to a particular location on the substrate, or to a capillary that may aspirate that portion of the stream off of the microfluidic hub. The detector may identify another portion of the stream as not of interest, and the electrodes on the substrate may accordingly be activated to direct that portion to a different location. In such examples, the portion of the separated sample which may be collected in a given droplet may depend on the critical actuation volume needed to allow digital microfluidic actuation, typically on the order of a few microliters. Depending on the critical actuation volume, the resolution of the separation, the resolution with which fluid is delivered to the fixture, and the width of the separation peaks of interest, the fixture may also allow broad separation peaks to be subsampled into droplets containing slower and faster moving constituents.

This same binning approach may be applied to a concentrated slug of some species of interest which may gradually dilute through axial diffusion and dispersion as it traverses a fluidic system. As a slug of interest passes the detector, a roughly Gaussian concentration profile may be observed. By properly synchronizing droplet collection at the fixture with the detector output, droplets of the background solvent may be separated from droplets corresponding to the tail regions of the Gaussian distribution and those associated with the peak regions of the slug. The result is a serially gathered collection of droplets discretely capturing different segments of the concentration profile. Droplet subsamples corresponding to the peak of this distribution may be concentrated relative to the total volume of fluid passed through the system.

While designed for capillary tubes, the in-plane capillary ferrules described above may be used with other elements, for example fiber optics. Many examples of optical diagnostics applied to droplets on substrates may operate by looking through one or both substrates in a fixture to interrogate the volume of the droplet. However, any light traveling through the thickness of the substrate-droplet-substrate stack may be subject to a series of refractive index transitions (e.g., air, glass, ITO, parylene, Teflon, droplet, Teflon, ITO, glass, air). The optical path length through the thickness of the droplet may be relatively short (e.g. <200 microns) compared to its lateral dimensions (e.g. 2.5 mm). Placing an in-plane fiber optics through one of the ferrules described above in the fixture, may advantageously allow optical energy to be passed through the thickest dimension of the droplet. Moreover, in-plane fibers may avoid or reduce complications associated with multiple intervening materials and their various refractive indices. In some examples, optical fibers may be placed directly in contact with a droplet between substrates on a fixture, which may minimize or reduce refractive index mismatch issues and even may lessen effects associated with the curvature of the droplet side-wall meniscus. Referring back to FIG. 12A, a fiber optic may be positioned through a port in a fixture such that a tip of the fiber optic may be proximate the electrode 1223 (or any other electrode shown in other examples). A droplet may be moved to the electrode 1223 using digital microfluidic technology described herein (e.g. sequentially activating electrodes along the path to the electrode 1223), bringing the droplet into view of the fiber optic. Fibers may be used to deliver and collect illumination in-plane or in conjunction with out-of-plane illuminators or detectors in some examples. Moreover, for fibers in direct contact with a droplet containing constituents of interest, near-field optical techniques may be applied to evaluate chemical or spectroscopic properties of analytes adsorbed directly onto the end of the glass fiber.

Figures 15A, 15B:
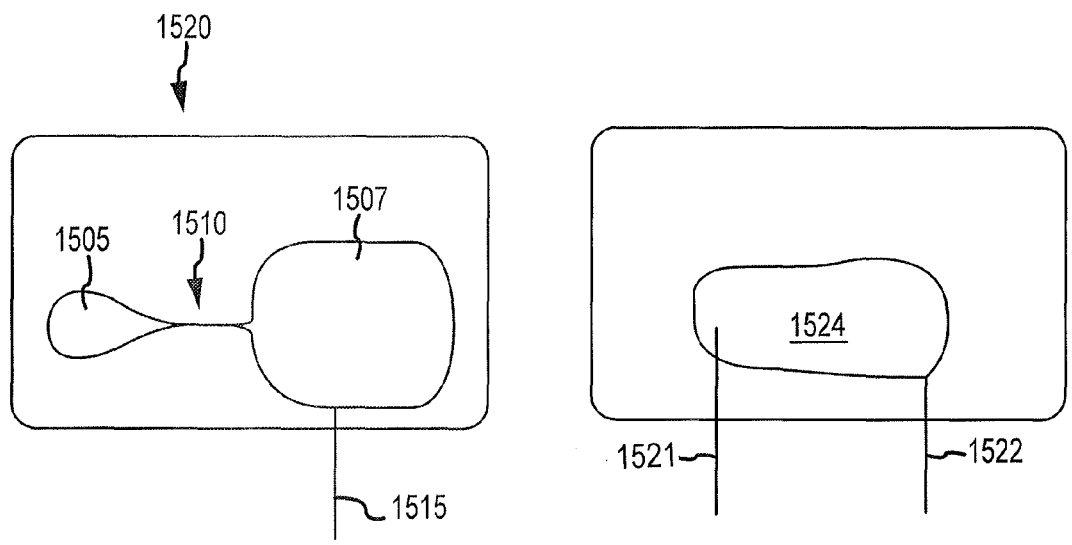
FIGS. 15A and 15B are schematic illustration of two virtual channels in accordance with embodiments of the present invention.

Embodiments of microfluidic hubs and systems in accordance with the present invention may be configured to utilize virtual channels. FIGS. 15A and 15B are schematic illustration of two virtual channels in accordance with embodiments of the present invention. A virtual channel refers to a channel defined not by physical device surfaces, but by the confines of a fluid bolus. In FIG. 15A, a virtual channel formed between two droplets or a critical droplet bridged to a fluid conduit access port by a spanning fluid stream is shown. A virtual channel may be formed when droplet 1505 is pulled away from the droplet 1507. When the fluid droplet contains a surfactant, a trail 1510 may be developed between the two droplets, which may allow for transport of analytes or other particles in the fluid between the two droplets. In some examples, a fluid conduit (e.g. capillary 1515) may still be attached to the droplet 1507, anchoring the droplet 1507, while the droplet 1505 is pulled away. Such a droplet-to-droplet virtual channel may be formed within example microfluidic hubs of the present invention, as illustrated schematically by microfluidic hub 1520 of FIG. 15A. For example, referring back to FIG. 12A, a droplet may be present on the electrode 1223. In some examples, the droplet may be fixed to the electrode 1223 (e.g. by providing a hydrophilic surface on the electrode 1223 or activating the electrode 1223). A droplet may be split from the droplet on the electrode 1223 (e.g. by activating a neighboring electrode). As a droplet moves away from the electrode 1223, trying to break free of the larger droplet on the electrode 1223, a trail as shown in FIG. 15A may form. The trail may be used to transport particles (e.g. magnetic beads), live cells, or other solid substances from one droplet to the other through the necked-down region which is can be directly interrogated by a point-source (e.g. laser) for ascertaining the specific properties (e.g. scattering, fluorescence emission).

Another type of virtual channel is an inlet-to-outlet channel, shown in FIG. 15B. One fluid conduit (e.g. capillary 1521) may be coupled to a fluid source to provide fluid into a space between substrates in an example fixture described herein. Another fluid conduit (e.g. capillary 1522) some distance away may be coupled to a second syringe-pump or other pressure source to aspirate the fluid. Accordingly, a fluid bolus 1524 (e.g. a virtual channel) may be formed between the two capillaries 1521 and 1522. By matching the flow rates at inlet and outlet capillaries 1521 and 1522, the bolus or compound droplet may be maintained at a fixed size while pressure driven flow circulates fluid through the capillary 1521, through virtual channel, and into the collector capillary 1522. Fluid addition may be accomplished by standard pumping or metering methods (e.g. syringe pump), while fluid removal can be achieved by pump or by simply connecting a suitably throttled vacuum line to the outlet capillary 1522. Beyond simply establishing the virtual channel by positioning droplets, actuation of underlying electrodes may control virtual channel morphology and/or routing once the virtual channel is communicating with matched inlet and outlet flows. This approach may enable functions such as continuous flushing or washing of electrodes in examples of fixtures described herein, which may eliminate or reduce biofouling and may prevent or reduce cross-contamination when the same set of electrodes may be used for subsequent experiments. Similarly, continuous flow virtual channels may be switched in real time to sweep different paths or sets of electrode pads. The ability to provide substantial flux of liquid on example fixtures described herein may facilitate the use of virtual channel flows to affect heat transfer on the fixtures.

As an example, local heating may be provided on one part of a substrate in a fixture described herein, and it may be desirable to introduce a virtual channel flow of cold water at another location to act as a heat sink, effectively isolating that heated zone from the rest of the substrate. Accordingly, continuous delivery of liquid at a pre-established temperature through one or more virtual channels may provide an option for on-fixture temperature control which may not require on-chip resistive heating or thermoelectric elements. Finally, contacting a discrete droplet to an established continuous flow virtual channel may facilitate liquid-liquid extractions on-chip, dilutions, or mixing via shear-induced flow recirculation.

With suitably matched inlet and outlet flows, in some examples, continuous virtual channel flow may be driven through the droplet-to-droplet virtual channel depicted in FIG. 15 (A). Since the thin stringer is formed by attempting to split a larger droplet into two smaller droplets (with surfactant in the liquid), a droplet splitting operation may be used to link inlet and outlet capillaries (or through-holes) before inlet and outlet flows are established, allowing pressure driven flow to occur in the necked-down region.

Microfluidic hubs and systems in accordance with embodiments of the present invention may be used in electrophoretic separations. An in-plane fluid conduit (e.g. capillary) may be filled with a polymer matrix and a wire nearby to complete an electrical circuit for use in performing electrophoretic separation. Accordingly, a fluid may be aspirated using droplets into the capillary from a microfluidic hub described herein, separated, and separated portions returned to the microfluidic hub and manipulated as desired. In-plane capillary and through-hole interfaces presented may enable direct coupling between on-fixture droplets and off-fixture electrophoretic separation systems in a closed-format digital microfluidic system. A substrate electrode, e.g. a ground plane electrode provided on the substrate 212 of FIG. 2A, even if coated with Teflon AF or other hydrophobic coating, may allow sufficient leakage current to act as an anode in an electrophoretic separation. While Teflon integrity and hydrophobicity appear to be unaffected, over time the area providing the anode contact may discolor visibly, suggesting surface fouling or other electrochemical processes may be degrading the electrical contact. Other examples for providing the fixture-side electrophoretic electrode include 1) coupling a Teflon-coated platinum wire through one of the in-plane capillary ports to make contact with the droplet, 2) fabricating dedicated EP electrode features on a substrate in the fixture, or 3) coupling an off-chip anode to a droplet in the fixture using a salt bridge fluidic electrochemical connection made through a second in-plane capillary (or through-hole via). With properly patterned electrodes on the substrate in a fixture (or suitably positioned wire electrodes), separations may also be accomplished by electrophoresing analytes from one on-fixture droplet, through a capillary loop past a detector, and back into a terminal on-fixture droplet. Wires with specialized coatings or particular wire types (e.g. Ag/AgCl) may be used in some examples for electrochemistry or electrochemiluminescence applications inside of droplets.

Beyond options for microfluidic hub-to-capillary electrophoresis, examples of microfluidic hubs and systems described herein also may be used to conduct electrophoretic separations on the microfluidic hub itself. In one example, a thin stringer between surfactant stabilized droplets (e.g. as shown in FIG. 15A), may act as the separation channel when a voltage differential is applied between the two droplet lobes. In a second example, extended droplets containing a suitable separation gel matrix may provide the medium for separation, again when a suitable voltage is applied across the long axis of the extended droplet. Another example includes a patterned gel bridge connecting two electrodes on a substrate in an example fixture. The outside of the bridge may be coated so as to be hydrophobic, but its hydrophilic ends may be exposed so that when droplets are positioned on the pads at either end of the bridge and voltage is applied, analytes may migrate through the bridge from one droplet to the other.

Examples of microfluidic hubs and systems described herein may be used to perform flow cytometry. As noted above in with reference to FIG. 15A, bridges (e.g. stringers) may be generated between droplets in the process of performing a droplet splitting operation in a fixture. In flow cytometry, particles of interest (e.g. cells, viruses, micro/nanoparticles, etc.) are made to flow in single file past a detector, which typically interrogates the particles on the basis of fluorescence or other optical properties. In some examples, cytometry produces a count of particles transiting the detection region, but the particle-by-particle nature of the method also makes it possible to classify, characterize, and even sort particles based on measurable criteria.

Conventionally, a flow cytometer is a large, expensive instrument which accomplishes single-file particle transport through hydrodynamic flow focusing, a technique in which a particle-laden sample is injected into the center of a flow channel and a higher velocity/flow-rate sheath flow is injected to either side of (in a 2D system) or around (in a coaxial system) the core sample flow. As a result of the velocity mismatch between the core and sheath flows, viscous shear tends to accelerate the core flow to match the much higher velocity of the sheath flow, effectively squeezing and shrinking the core flow in the lateral or radial directions and stretching or elongating it in the axial direction. In addition to forcing the core flow into a smaller volume at the center of the channel, the thinning and stretching of the core flow stream has the effect of increasing the axial spacing between particles in the core flow, causing them to move downstream in a largely single-file fashion. By discretizing and serializing the particles in the sample, high-throughput particle-by-particle detection and characterization become possible. Such a system may have the disadvantages of requiring fairly large pumps, complex plumbing, and substantial quantities of sheath fluid to generate the desired particle throughput. Cytometric analysis of multiple samples is typically a serial operation, as most laboratories cannot afford a battery of the instruments to accomplish assays in parallel.

As an alternative to the expense and complexity of conventional cytometers, embodiments of the present invention may utilize the bridging behavior of surfactant-stabilized droplet-to-droplet stringers (as shown, for example in FIG. 15A) on a microfluidic hub described herein to provide the functionality of a flow cytometer. Such embodiments may be relatively less expensive, more compact, and more parallelizable than conventional cytometers. Referring back to FIG. 15A, a droplet containing a suspension of cells or particles of interest may be moved into position and merged to a larger droplet 1507. The larger droplet may be pinned in place by surface tension forces, electrode actuation, or the presence of a capillary, as described above. Next, the sample-containing portion of the combined droplet 1505 may be actuated away from the anchored larger droplet, forming a thin meniscus stringer 1510 joining the two droplets. When the electrode actuating the sample-containing droplet is deactivated, the surface energy imbalance between the larger and smaller droplet lobes (and the fact that the larger droplet is pinned in place) may cause the smaller droplet to shrink and move inward toward the larger droplet as fluid flows through the stringer into the larger lobe (FIG. 13C). By repeatedly cycling the electrode to maintain the position of the smaller droplet lobe, all fluid (and sample particles) may eventually be pumped through the stringer in substantially serial fashion from the smaller to the larger lobe. By situating a suitable detector to observe the transit of the sample particles through the stringer, this quasi-passive pumping process approximates the functionality of a flow cytometer on examples of fixtures according to the present invention. It should be noted that while FIG. 15A depicts a relatively short stringer, it may be possible to create and sustain very high aspect ratio droplet-to-droplet bridges exceeding 1 cm in length.

Variations on this flow cytometry approach are also possible. Functionalized magnetic beads may be collected by magnetic forces at one end of a droplet, the magnet removed, and the droplet split as in the preceding discussion to cause a gradual pumping of the beads across a droplet stringer for analysis. In the case of a magnetic bead based assay, the cytometry operation may be repeated as desired to improve the statistical significance of the measurement or observe time-dependent processes. Core-sheath flow structures may be approximated by surrounding a sample containing droplet with a larger volume of sample-free solution, then quasi-passively pumping from that concentric composite droplet into a larger receiving droplet as described.

Examples of on-hub cytometry processes described herein may advantageously be readily parallelized simply by actuating a plurality of droplet pairs simultaneously on the same microfluidic hub. This kind of parallelized functionality may enable in situ cytometric analysis on a hub-based cell culture platform, for instance. Either a plurality of detectors or a scanning/multiplexing scheme may be employed to enable interrogation of multiple regions of the device with a sufficiently high sampling rate to capture particle transit events in multiple stringers. Additionally; functionalities may also be provided. For example, droplet position and size may be readily evaluated using impedance measurements. Making such measurements in real-time while the quasi-passive pumping process is occurring may provide the opportunity to implement closed-loop feedback control to automate the determination of when and how often to re-actuate the source droplet to maintain essentially steady-state pumping. Furthermore, Coulter-counter like functionality may be provided where each particle transit event generates a measurable change in the electrical impedance through the stringer. This change in impedance may enable counting or even sizing measurements made using impedance sensors and circuitry coupled to the electrodes of example substrates, some or all of the measurement circuitry may be provided by printed circuit boards of example fixtures and microfluidic hubs described herein.

Example microfluidic hubs and systems according to the present invention may further provide capillary-enabled isoelectric focusing. Isoelectric focusing is a separation process used to separate proteins and other biomolecules. A sample containing species to be separated is introduced into a medium within which a fixed pH gradient is established (typically a gel), and voltage is applied across the gradient medium using salt-bridges or external electrodes in contact with the working fluid. Because molecular net charge depends upon the local pH of the surrounding medium, proteins or other molecules will tend to migrate through the pH gradient matrix under the influence of the electric field (e.g. net positive molecules moving toward the anode, etc.) until they reach a position where the local pH leaves them with a net zero charge, where they stop migrating. The pH at this location defines the isoelectric point for a given molecule, and the fact that different proteins have different isoelectric points means that distinct species can be spatially separated from a heterogeneous sample.

Figure 16:
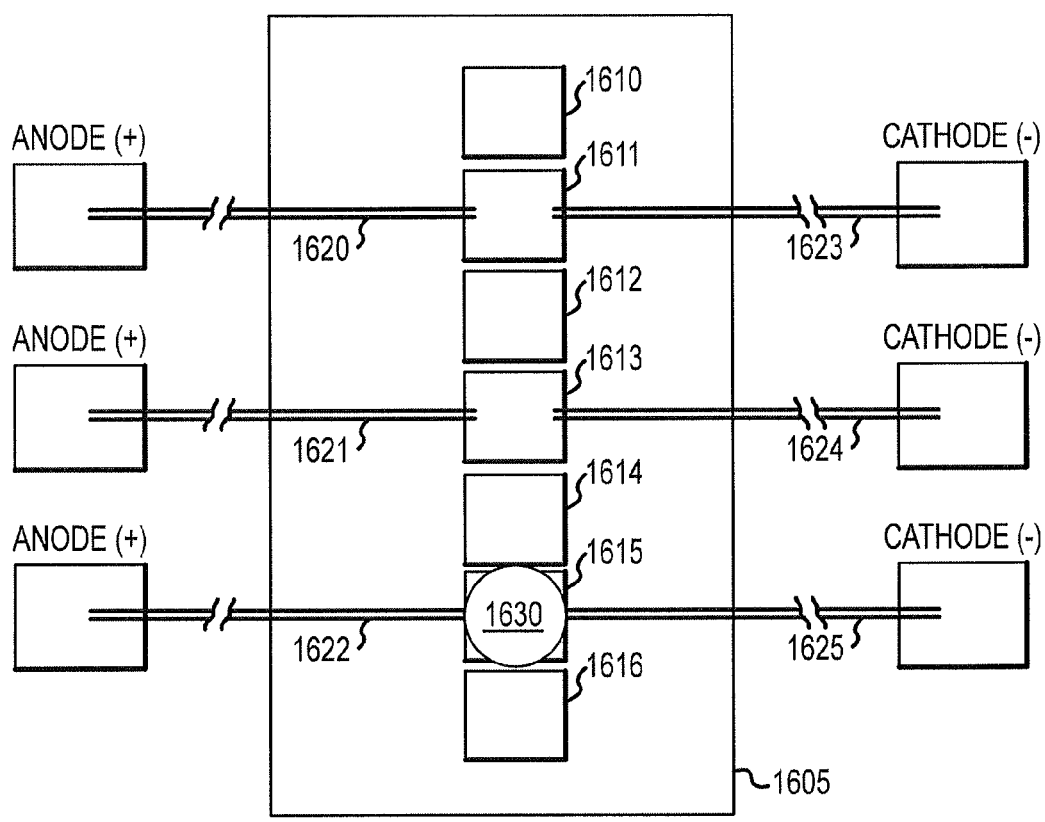
FIG. 16 is a schematic illustration of a microfluidic hub in accordance with an embodiment of the present invention that may be used for isoelectric focusing.

FIG. 16 is a schematic illustration of a microfluidic hub in accordance with an embodiment of the present invention that may be used for isoelectric focusing. For example, a fixture 1605 may include a surface having electrodes 1610-1616. The fixture 1605 may include access ports having fixed capillaries 1620-1625 entering into a space between surfaces. In one example with our system, two capillaries 1622 and 1625 may be positioned opposite of each other with their tips within the boundary of a single electrode 1615. A droplet 1630 may be actuated onto the electrode 1615 to contact the two capillaries 1622 and 1625 to maintain fluidic and electrical communication with both capillaries. The capillaries 1620-1625 may be filled with a specified range of immobilized pH gradients, with for example the capillary 1620 having a pH gradient <6.0, the capillary 1621 having a pH gradient <6.5, the capillary 1622 having a pH gradient <6.8, the capillary 1625 having a pH gradient >7.2, the capillary 1624 having a pH gradient >7.5, and the capillary 1623 having a pH gradient >8.0. Other numbers of capillaries or division of pH spectrum across the capillaries may be used in other examples. An external electrical field gradient may be applied (e.g. using a voltage source) to the prefilled capillaries. With the electrical field turned on, only the positive or negatively charged proteins or protein conjugates (or other charged particles) in the droplet 1630 may migrate towards the capillary with the appropriate charge and migrate towards their isoelectric points in the specified range. So, for example, if the droplet 1630 was actuated to the electrode 1611, and electric field applied between the capillaries 1620 and 1623, species in the droplet having a pH <6.0 may be drawn into the capillary 1620 from the droplet while species in the droplet having a pH >8.0 may be drawn into the capillary 1623 from the droplet. Accordingly, the droplet may then continue to contain only species having a pH between 6.0 and 8.0. The same droplet may be actuated to a second position (e.g. the electrode 1613) in the middle of two capillaries that has a narrower pH gradient range (e.g. the capillaries 1621 and 1624) to further remove proteins of noninterest. This procedure can continue multiple times until the protein or range of proteins of interest is remaining in the droplet. For example, the droplet 1630 then between the capillaries 1622 and 1625 after applying an electric field between the capillaries 1622 and 1625 may include only species having a pH between 6.8 and 7.2. Using this system of capillaries and droplet interface with the microfluidic hub, the protein (or other species) mixture can be fractionated to select the protein of interest or uninterested interfering proteins removed.

Embodiments of microfluidic hubs described herein may be used to conduct isoelectric focusing separations. Two in-plane capillaries may be provided installed opposite one another and positioned such that their facing open ends are proximate an electrode onto which sample droplets can be moved. The capillaries may be pre-loaded with a gel or other matrix enabling the establishment of the pH gradient required for isoelectric focusing, where one capillary contains a lower end of the gradient and the other contains a solution having a pH at the upper end. Electrodes in electrical communication with the capillaries across the fluid may apply of a bias voltage across the two segments of the pH gradient matrix when a droplet is moved into position, bridging the two capillaries and effectively completing an electrochemical circuit. With a droplet of neutral pH positioned between the capillaries and the voltage applied, proteins or other biomolecules in the droplet may migrate along the now-completed pH gradient based on their induced charge and the action of the electric field through the capillaries and the drop. Once segregated in the gradient matrix of the two capillaries, the sample droplet may be moved away and a new droplet introduced to allow subsequent separations or elution of the separated species from one or both capillaries into the new droplet.

From the foregoing it will be appreciated that, although specific embodiments of the invention have been described herein for purposes of illustration, various modifications may be made without deviating from the spirit and scope of the invention.

What is claimed is:

1. A microfluidic hub comprising:
   a substrate;
   a frame, wherein the frame defines a registration surface configured to receive the substrate and position the substrate a predetermined distance from another surface, wherein the frame defines a plurality of access ports positioned for access to a space between the substrate and the another surface;
   a fluid conduit positioned in one of the plurality of access ports, wherein the fluid conduit is in fluid communication with the space between the substrate and the another surface, wherein the fluid conduit is positioned to deliver a fluid droplet to the space between the substrate and the another surface, from the space between the substrate and the another surface, or both; and a droplet actuator configured to move the fluid droplet within the space between the substrate and the another surface.

2. The microfluidic hub of claim 1, wherein the frame provides the another surface.

3. The microfluidic hub of claim 1, wherein the substrate further includes electrodes on the substrate and a hydrophobic material on the electrodes, wherein the electrodes are arranged in a path and have a size configured to transport the fluid droplet on the hydrophobic material from an area near one of the plurality of electrodes to another in response to a control signal.

4. The microfluidic hub of claim 1, wherein the fluid conduit comprises a first fluid conduit, and the microfluidic hub further comprises a second fluid conduit, wherein the droplet actuator is arranged to transport the fluid droplet from the first fluid conduit to the second fluid conduit.

5. The microfluidic hub of claim 1, wherein the fluid conduit is positioned laterally in the space between the substrate and the another surface such that the fluid droplet is not transported through the substrate or the another surface by the fluid conduit.

6. The microfluidic hub of claim 1, wherein the substrate is a first substrate, the registration surface comprises a first registration surface, the another surface is a surface of a second substrate, and wherein the frame further defines a second registration surface configured to receive the second substrate.

7. The microfluidic hub of claim 6, wherein neither the portion of the frame defining the first registration surface nor the portion of the frame defining the second registration surface has a thickness equal to the predetermined distance.

8. The microfluidic hub of claim 6, wherein the portions of the first and second substrates received by the registration surfaces do not overlap one another, and wherein portions of the substrates that are not pressed against the registration surfaces do overlap one another within the space between the substrates.

9. The microfluidic hub of claim 1, wherein an object is positioned in one of the plurality of access ports, and wherein the object is selected from the group consisting of a capillary, a tube, a needle, an electrode, a fiber, an optical fiber, a filament, a wire, a wicking structure, a thermocouple, a heater, a resistive temperature detector, a conductive rod or shaft, a resistor, a capacitor, an inductor, a transistor, an electrical component, a coil, a magnet, an electromagnet, a solenoid, a rotary shaft, a piezoelectric element, a thermoelectric element, a diode, a photodiode, a phototransistor, an ultrasonic transducer, an articulated probe tip, a micromanipulator, a waveguide, a Fabry-Perot interferometer, a surface plasmon resonance probe, and a surface enhanced Raman spectroscopy probe.

10. The microfluidic hub of claim 1, further comprising electrical contacts on the registration surface coupled to conductive pads on the substrate.

11. A system comprising:
a microfluidic hub comprising:
    a fixture configured to define a space between two surfaces, wherein the fixture further defines access ports for interfacing to the space between two surfaces;
    a first fluid conduit positioned in one of the access ports, wherein the first fluid conduit is in communication with the space between two surfaces;
    a second fluid conduit positioned in another one of the access ports, wherein the second fluid conduit is in communication with the space between two surfaces; and
    a droplet actuator configured to move a fluid droplet within the space between the two surfaces;
a first fluid module coupled to the first fluid conduit, wherein the first fluid module is in fluid communication with the microfluidic hub through the first fluid conduit;
a second fluid module coupled to the second fluid conduit, wherein the second fluid module is in fluid communication with the microfluidic hub through the second fluid conduit;
a power source configured to provide power to the droplet actuator responsive to control signals;
a controller configured to provide the control signals to the power source to activate the droplet actuator to move a fluid droplet received from the first fluid conduit through the microfluidic hub to the second fluid conduit; and
a user interface configured to communicate with the controller for user operation of the system.

12. The system of claim 11, wherein the droplet actuator includes a plurality of electrodes on at least one of the two surfaces and a hydrophobic material covering the plurality of electrodes.

13. The system of claim 12, wherein the fixture further comprises external electrical connectors coupled to the plurality of electrodes, and wherein the power source is configured to provide power to selected ones of the electrodes responsive to the control signals.

14. The system of claim 13, wherein the user interface comprises a touchscreen configured to display a representation of the electrodes, and wherein the user interface is further configured to provide an indication to the controller of a selected electrode, and wherein the controller is further configured to respond to the indication of the selected electrode by applying a predetermined voltage to the selected electrode.

15. The system of claim 11, wherein the controller is further configured to control a pump, valve, or both, to cause the fluid droplet to be aspirated into the second fluid conduit and travel to the second fluid module.

16. The system of claim 11, wherein at least one of the first or second fluid modules comprises a continuous flow module, and wherein the droplet actuator employs digital microfluidic technology configured for movement of discrete droplets.

17. A method for interfacing fluid modules, the method comprising:
    introducing a droplet of fluid to a space between two surfaces through a first fluid conduit inserted into the space between the two surfaces;
    moving the droplet along a substrate, wherein the droplet is constrained between the two surfaces;
    moving the droplet to a location proximate a second fluid conduit inserted into the space between the two surfaces; and
    drawing the droplet at least partially into the second fluid conduit.

18. The method of claim 17, further comprising drawing a particle from or moving a particle within the droplet based on a property of the particle.

19. The method of claim 17, wherein the first fluid conduit is coupled to a first fluid module, and the second fluid conduit is coupled to a second fluid module.

20. The method of claim 17, wherein said introducing comprises developing the droplet at an end of the first fluid conduit; and wherein said method further comprises:
    transporting a second droplet to the end of the first fluid conduit such that the droplet merges with the second droplet.

21. The method of claim 20, wherein said moving the droplet along the substrate comprises activating an electrode on the substrate and wherein the droplet at the end of the first fluid conduit is too small to be moved in response to activation of the electrode.

* * * * *